United States Patent [19]
Levery et al.

[11] Patent Number: 6,083,929
[45] Date of Patent: *Jul. 4, 2000

[54] EXTENDED TYPE 1 CHAIN GLYCOSPHINGOLIPIDS AS TUMOR-ASSOCIATED ANTIGENS

[75] Inventors: Steven B. Levery, Seattle; Sen-itiroh Hakomori, Mercer Island; Mark R. Stroud, Seattle, all of Wash.

[73] Assignee: The Biomembrane Institute, Seattle, Wash.

[ * ] Notice: This patent is subject to a terminal disclaimer.

[21] Appl. No.: 08/174,166

[22] Filed: Dec. 29, 1993

Related U.S. Application Data

[63] Continuation-in-part of application No. 07/888,564, May 22, 1992, abandoned, which is a continuation-in-part of application No. 07/695,506, May 6, 1991, abandoned.

[30] Foreign Application Priority Data

May 6, 1992 [WO] WIPO .................... PCT/US92/03842

[51] Int. Cl.$^7$ .......................... A61K 31/715; C08B 37/00

[52] U.S. Cl. ................................ 514/54; 514/23; 514/53; 536/53; 536/55.1; 536/55.2; 536/55.3

[58] Field of Search ................................ 514/23, 53, 54; 536/53, 55.1, 55.2, 55.3

[56] References Cited

U.S. PATENT DOCUMENTS

| | | | |
|---|---|---|---|
| 5,011,920 | 4/1991 | Hakomori et al. | 536/53 |
| 5,030,723 | 7/1991 | Nudelman et al. | 536/53 |

OTHER PUBLICATIONS

Macher et al; J. Biol. Chem. 256(4):1968–1974 (1981), months not available.
Gooi et al; Nature 292:155–158 (1981), months not available.
Dabrowski et al; Arch. Biochem. Biophys. 210(1):405–411 (1981), months not available.
Magnani et al; Cancer Research 43:5489–5492 (1983), months not available.
Childs et al; The EMBO Journal 3(10):2227–2233 (1984), months not available.
Fenderson et al; J. Exp. Med. 160:1591–1596 (1984), months not available.
Kannagi et al; J. Biol. Chem. 260(10):6410–6415 (1985), months not available.
Khare et al; Carb. Res. 136:285–308 (1985), months not available.
Holmes et al; J. Biol. Chem. 260(12):7619–7627 (1985), months not available.
Levery et al; Carb. Res. 151:311–328 (1986), months not available.
Levery et al; Carb. Res. 178:121–144 (1988), months not available.
Holmes et al; Arch. Biochem. Biophys. 274(2):633–647 (Nov. 1. 1989).
Stroud et al; J. Biol. Chem. 266(13):8439–8446 (May 5, 1991).
Bouhours et al; J. Biol. Chem. 266(28): 18613–19 (Oct. 5, 1991).
Iwamori et al. FEBS Letters 1988, 233(1), 134–138, months not available.
Nozawa et al. Cancer Research 1989, 49, 6401–6406, months not available.

*Primary Examiner*—Kathleen K. Fonda
*Attorney, Agent, or Firm*—Roylance, Abrams, Berdo & Goodman, L.L.P.

[57] ABSTRACT

A variety of compounds are provided which are usefdl as immunogens and as tumor markers. The present invention discloses methods relating to the detection of cancer. Extended forms of the lacto-series type 1 chain are shown to be present in various cancer tissues. The present invention also provides a cell line and the monoclonal antibody produced therefrom. Such an antibody has a number of uses, including in diagnostic or therapeutic methods.

9 Claims, 17 Drawing Sheets

EXTENDED TYPE 1 CHAIN GLYCOSPHINGOLIPIDS AS TUMOR-ASSOCIATED ANTIGENS

CROSS REFERENCE TO RELATED APPLICATION

This is a Rule 62 Continuation-in-Part of application Ser. No. 07/888,564, filed May 22, 1992 (abandoned), which is a Continuation-in-Part application Ser. No. 07/695,506, filed May 6, 1991 (abandoned).

TECHNICAL FIELD

The present invention relates generally to new human tumor associated antigens. This invention is more particularly related to extended type 1 chain glycosphingolipids and their uses, e.g., as inmunogens and as tumor markers.

BACKGROUND OF THE INVENTION

Despite enormous investments of financial and human resources, cancer remains one of the major causes of death. Current cancer therapies cure only about 50% of the patients who develop a malignant tumor. In most human malignancies, metastasis is the major cause of death.

Metastasis is the formation of a secondary tumor colony at a distant site. In most human malignancies, distant metastases are often too small to be detected at the time the primary tumor is treated. Furthermore, widespread initiation of metastatic colonies usually occurs before clinical symptoms of metastatic disease are evident. The size and age variation in metastases, their dispersed anatomical location, and their heterogeneous composition are all factors that hinder surgical removal and limit the concentration of anti-cancer drugs that can be delivered to the metastatic colonies. Therefore, detection of malignancies prior to dissemination of the tumor cells from the primary site is needed to enhance the effectiveness of current cancer therapies.

Aberrant glycosylation has been observed to be a common feature for most cancer types. Most of the carbohydrate antigens used for the diagnosis of human cancers carry polylactosamine stnictures, i.e., they contain Galβ1→3/4GlcNAc. Polylactosamines are usuallv classified into two categories according to their polylactosamine unit structure. The polylactosamine having the Galβ1→3GlcNAc structure is called the type 1 chain, and that having the Galβ1→4GlcNAc structure is referred to as the type 2 chain. The most common tumor-associated antigens found in major human cancers have the lacto-series type 2 chain structure, which usually has been sialylated and/or fucosylated. Type 1 chain antigens are abundant in normal cells and tissues, and also are cancer-associated. For example, 2–3 sialylated Le$^a$ antigen (the CA 19-9 antigen defined by the N19-9 antibody) is a cancer-associated type 1 chain antigen. However, cancer diagnostic methods based on the detection of these known antigens have been hampered by high false positive and/or high false negative incidences.

Due to the dffficulties in the current approaches to the diagnosis of cancer, there is a need in the art for improved compositions and methods. The present invention fills this need, and further provides other related advantages.

SUMMARY OF THE INVENTION

Briefly stated, the present invention provides isolated compounds and methods of screening for cancers by detecting such compounds. In one aspect, the present invention provides an isolated compound, with or without fucosyl and/or sialyl residues, having the formula:

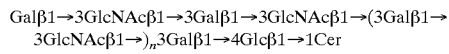

wherein n is 0 or an integer of 1 or more, there are at least two fucosyl and/or one or more sialyl residues, Gal represents galactose, Glc represents glucose, GlcNAc represents N-acetylglucosamine, Cer represents a ceramide, and wherein said at least two fucosyl residues are linked to the GlcNAc residues via an α1→4 linkage and/or to the terminal Gal residue via an α1→2 linkage and said one or more sialyl residues are linked to the terminal Gal residue via an α2→3 linkage and/or to one or more of the subterminal GlcNAc residues via an α2→6 linkage.

In a further aspect, the present invention provides the above-described isolated compound having the formula:

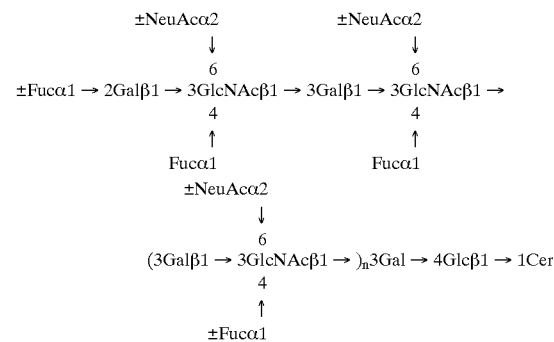

wherein Fuc represents fucose and NeuAc represents N-acetylneuraminic acid.

In another aspect the invention provides the first-described compound having the formula:

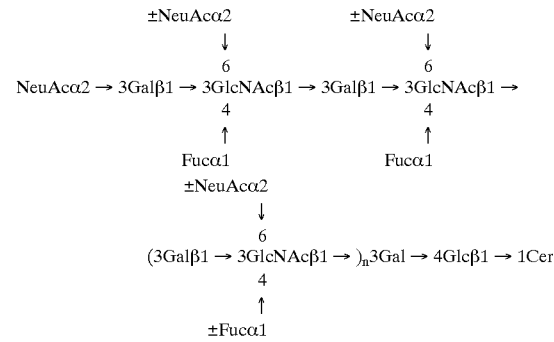

wherein Fuc represents fucose and NeuAc represents N-acetylneuraminic acid.

In another aspect the invention provides the first described compound having the formula:

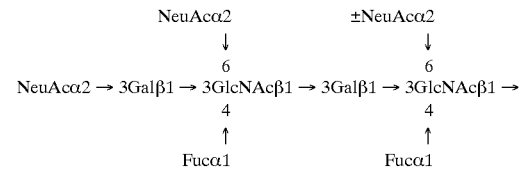

-continued

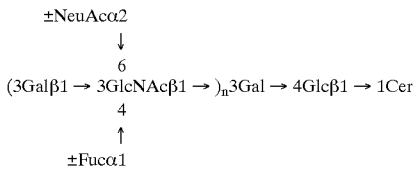

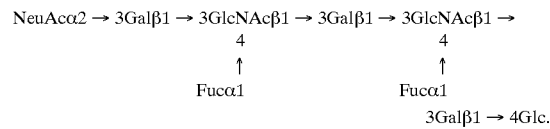

wherein Fuc represents fucose and NeuAc represents N-acetylneuraminic acid.

In one embodiment, the present invention provides an isolated compound having the formula:

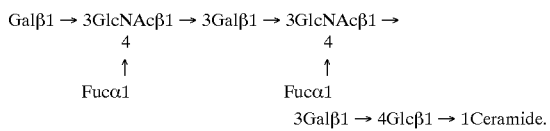

In another embodiment, the present invention provides an isolated compound having the formula:

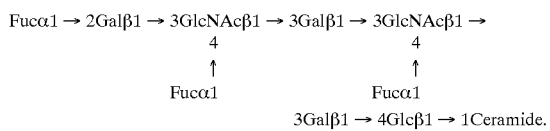

In an even further embodiment, the present inv-ention provides an isolated compound having the formula:

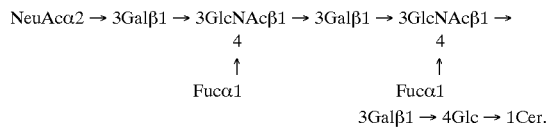

Within a related aspect, the present invention provides an isolated compound comprising an epitope having the formula:

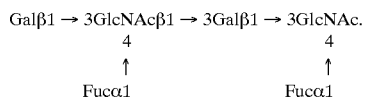

Within another related aspect, the present invention provides an isolated compound comprising an epitope having the formula:

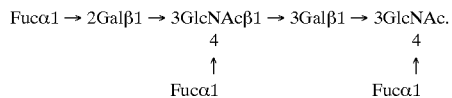

Within an even further aspect, the present invention provides an isolated compound comprising an epitope having the formula:

In yet other aspects, any of the compounds of the present invention may be used as an immunogen for the production of polyclonal or monoclonal antibodies.

In another aspect of the present invention, methods for screening for cancer are provided. The methods comprise the steps of: (a) isolating a biological sample from a warm-blooded animal; and (b) testing the sample for the presence or amount of a compound according to formulae I, II, III, IV, V or VI.

Within a related aspect, the present invention provides the cell line IMH2, as designated by ATCC No. HB 11026, and the monoclonal antibody produced by the cell line (MAb IMH2).

These and other aspects of the present invention will become evident upon reference to the following detailed description and attached drawings.

DETAILED DESCRIPTION OF THE INVENTION

Figure 1A:
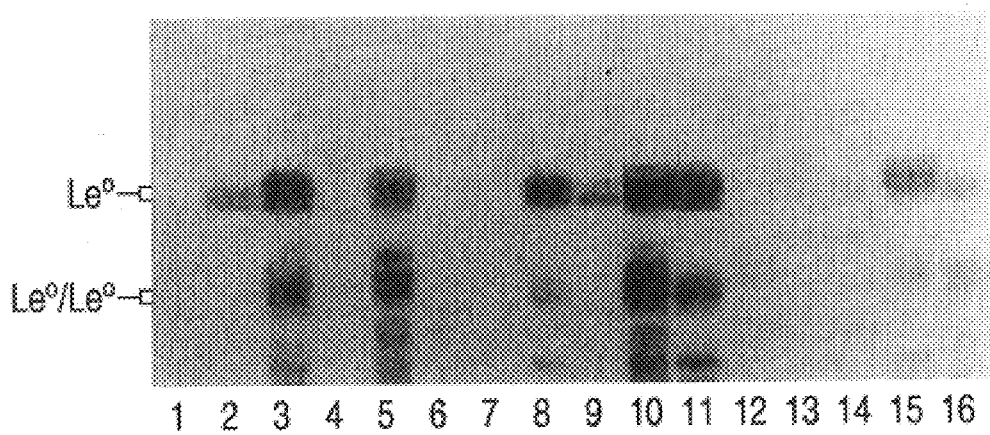
FIG. 1 shows the results of HPFTLC immunostaining of upper neutral glycoilpids with MAb NCC-ST-421. Panels A and B, neutral glycolipids from various tumors. Lanes 1–20 and 26–28, glycolipids were obtained from liver adenocarcinoma originating from the primary lesion indicated. Lanes 1–5 and 8–11, colon; lanes 6, 7, 12–14, 26–28, lung; lane 15, breast; lane 16, Hodgkin's disease; lanes 17–19, gall bladder; lane 20, prostate; lane 21, renal cell carcinoma; lane 22, leiomyosarcoma; lane 23, embryonal rhabdomyosarcoina; lane 24, breast; lane 25, colon. Panel C, neutral glycolipids obtained from normal tissues. Lanes 1, 6, and 9, liver; lane 2, small intestine; lane 3, spleen; lanes 4–5, kidney; lane 7, pancreas; lane 8, placenta; lane 10, lung.

The present invention is generally directed towards compounds and methods relating to the detection of cancers. More specifically, the disclosure of the present invention shows that lacto-series type 1 chain occurs in extended forms in cancer tissues.

As noted above, type 1 chain lactosamine (Galβ1→3GlcNAc) is known to be abundant in normal cells and tissues. Although polylactosamine antigens having an extended type 2 chain (i.e., Galβ1→4GlcNAc core structure is repeated) have been detected, those with an extended type 1 chain have not been detected. Thus, lacto-series type 1 chain has traditionally been considered not to occur in extended form.

As disclosed within the present invention, extended forms of lacto-series type 1 chain (i.e., Galβ1→3GlcNAcβ1→[3Galβ1→3GlcNAcβ1→]$_n$3Galβ1→4GalβR, with or without sialyl and/or fucosyl residues) are present in cancer tissues. Two representative extended forms of lacto-series type 1 chain were isolated by subjecting a glycolipid fraction (extracted from tumor cells) to preparative column and thin layer chromatography. Structural determination (by enzymatic degradation, $^+$FAB-MS, methylation analysis and $^1$H-NMR spectroscopy) resulted in the identification of the glycosphingolipi(Is (GSLs), dimeric Le$^a$ (i.e., Le$^a$–Le$^a$), Le$^b$–Le$^a$ and extended sialyl Le$^a$ (sLe$^a$–Le$^a$). The GSL dimeric Le$^a$ has the structure:

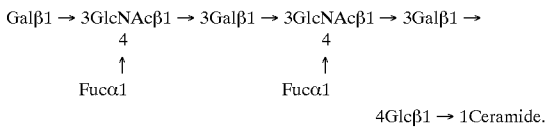

The GSL Le$^b$–Le$^a$ has the structure:

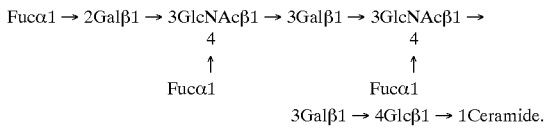

Ceramides (Cer) are sphingolipid bases which are acylated on the amine with a fatty acid.

A slow-migrating sialyl-Lewisa (sLe$^a$) active glycosphingolipid (GSL) was purified to homogeneity from the monosialyl ganglioside fraction of the colonic adenocarcinoma cell line Colo205. This compound was purified by HPLC and preparative HPTLC in two different solvent systems and stained strongly by TLC immunostaining using the α-sLe$^a$ monoclonal antibody (Mab) NKH-1. Mild acid hydrolysis (1% acetic acid, 100° C. for 1 hour) yielded a faster migrating component that co-migrated with a dimeric-Le$^a$ standard GSL and stained strongly by the α-dimeric Le$^a$ Mab ST-421. The structures was confirmed by $^1$H-NMR spectroscopy as sialyl-dimeric Le$^a$ (see structure below). This structure represents a novel tumor-associated GSL and a potential tumor marker.

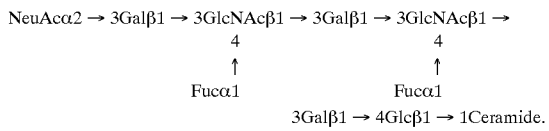

In addition to the particular glycolipids depicted above, the Le$^a$–Le$^a$ Le$^b$–Le$^a$ is Le$^a$–Le$^a$ epitopes may be present as extended type 1 chains with additional [3Galβ1→3GlcNAcβ1→]$_n$ units. Furthermore, the Le$^a$–Le$^a$ and Le$^b$–Le$^a$ epitopes may be carried by glycoproteins, e.g., high molecular weight mucin-like sera glycoproteins.

Given the teachings provided herein, it would be evident to those of ordinary skill in the art that other extended forms of lacto-series type 1 chain compounds may be isolated from biological starting materials, such as cancer tissue, or synthesized chemically (and/or enzymatically) following structural identification. Briefly, the structure of carbohydrates bound to either lipids or proteins may be determined based on degradation, mass spectrometry, including electron-impact direct-probe (EI) and fast atom bombardment (FAB), and methylation analysis (techniques described below and, for example, in Nudelman et al., *J. Biol. Chem.* 261:5487–5495, 1986). Degradation analysis may be accomplished chemically and/or enzymatically, e.g., by glycosidases. The carbohydrate sequence suggested by degradation analysis may be determined by methylation analysis (e.g., Hakomori, *J. Biochem.* 55:205–208, 1964) followed by chemical ionization mass spectrometry of permethylated sugars (e.g., Stellner et al., *Arch. Biochem. Biophys.* 155:464–472, 1974; Levery et al., *Meth. Enzymol.* 138:13–25, 1987). Alternatively, or in conjunction with these techniques, EI mass spectrometry may be performed on permethylated glycans or after the appropriate degradation of intact glycans (e.g., Kannagi et al., *J. Biol. Chem.* 259:8444–8451, 1984; Nudelman et al., *J. Biol. Chem.* 263:13942–13951, 1988). Homogeneity of the carbohydrate sequence may be demonstrated based on various chemical and physical criteria, including proton NMR spectroscopy of intact or methylated glycan and FAB mass spectrometry. Once a carbohydrate structure has been determined, the carbohydrate or derivatives thereof or non-carbohydrate functional equivalents thereof may be synthesized using techniques well known to those of ordinary skill in the art.

The compounds of the present invention may be used as immunogens for the production of polyclonal and monoclonal antibodies (MAbs). Polyclonal antibodies may be produced by standard mnethodologies. For example, briefly, polyclonal antibodies may be produced by immunization of an animal with a compound of the present invention and subsequent collection of its sera. It is generally preferred to follow the initial immunization with one or more boosters prior to sera collection. MAbs may be generally produced by the method of Kohler and Milstein (*Nature* 256:495–497, 1975; *Eur. J. Immunol.* 6:511–519, 1976). Briefly, the lymph nodes and/or spleens of an animal immunized with a compound of the present invention are fused with mnyeloma cells to form hybrid cell lines ("hybridomas" or "clones"). Each hybridoma secretes a single type of immunoglobulin and, like the myeloma cells, has the potential for indefinite cell division. An alternative to the production of MAbs via hybridomas is the creation of MAb expression libraries using bacteriophage and bacteria (e.g., Sastry et al., *Proc. Natl. Acad. Sci. USA* 86:5728, 1989; Huse et al., *Science* 246:1275, 1989). Selection of antibodies exhibiting a desired specificity may be performed in a variety of ways well known to those of ordinary skill in the art.

It may be desirable to combine a compound of the present invention with a carrier in order to increase their immunogenicity. Suitable carriers include inactivated bacteria, keyhole limpet hemocyanin, thyroglobulin, bovine serum albumin and derivatives thereof. For example, all or a portion of the carbohydrate residues of the GSLs Le$^a$–Le$^a$ or Le$^b$–Le$^a$ may be combined with a carrier. A compound of the present invention may be combined with a carrier by a variety of means, including adsorption and covalent attachment.

A representative example of the use of a compound of the present invention as an immunogen is the immunization of mice with Le$^b$/Le$^a$ antigen. In brief, Le$^b$/Le$^a$ isolated from Colo205 cells was combined with a suspension of acid-treated *Salmonella minnesotae,* injected via tail vein into Balb/c mice, and the injection repeated three times with 10-day intervals. Following the final injection, splenocytes of immunized mice were harvested and fused with myeloma cells. A hybridoma, IMH2, which showed preferential reactivity with the immunogen, was established and deposited with ATCC (American Type Culture Collection, 12301 Parklawn Dr., Rockville, Md. 20852 USA) as ATCC No. HB 11026. The hybridoma produces a MAb IMH2 with an $IgG_3$ isotype.

MAb IMH2 reacts not only with the inunumogen used, but also with $Le^y/Le^x$ antigen, and to a lesser degree with short-chain $Le^y$ or $Le^b$ with hexasaccharide ceramide (i.e., $IV^2FucIII^3FucnLc_4Cer$ or $IV^2FucIII^4FucLc_4Cer$). It showed high incidence of staning and strong reactivity with carcinomas of colon, rectum, liver, pancreas, and endometriu but no reactivity with normal colonic mucosa at various loci, and minimal reactivity with normal liver, pancreas, or uterine endometrium. Its expression in colorectal tumors and normal cecal tissue was independent of secretor status, whereas that in normal urothelium was dependent on secretor status. MAb IMH2 displayed strong lymphocyte-activated or complement-dependent killing of human colonic cancer Colo205 cells in vitro, and inhibition of Colo205 growth in vivo. Therefore, as disclosed within the present invention, a new extended type 1 chain structure, $Le^b/Le^a$, is a useful tumor marker associated with carcinomas of colon, rectum, pancreas, liver, and endometrium, and MAb IMH2 has diagnostic and therapeutic applicability for these carcinomas.

Methods for the detection of extended forms of type 1 chain antigen, such as $Le^a$–$Le^a$ and/or $Le^b$–$Le^a$ antigens, may be used to screen for cancers. For example, the GSL $Le^b$–$Le^a$ and the GSI $Le^a$–$Le^a$ were detected by TLC immunostaining with MAb IMM and MAb NCC-ST-421 (established according to Watanabe et al., *Jpn. J. Cancer Res, (Gann)* 7:43→52, 1985), respectively, of neutral glycolipid fractions prepared firom various tumor samples. Such samples include tissue from colonic cancer, breast cancer, Hodgkin's disease, gallbladder cancer and embryonal rhabdomyosarcoma The GSL $Le^a$–$Le^a$, for example, was not detected in glycolipid fractions from normal tissue from spleen, liver, kidney, placenta and lung. Given the teachings provided herein, it would be evident to those of ordinary skill in the art that a variety of means for detecting tumor-associated extended type 1 antigens (including the use of binding partners specific for tumor-associated extended type 1 antigens, such as GSL $Le^a$–$Le^a$ and $Le^b$–$Le^a$) could be employed within the methods of the present invention. For example, antibodies specific for $Le^a$–$Le^a$ or $Le^b$–$Le^a$ epitopes may be produced as described above, and the presence of immunocomplexes may be tested following contact (e.g., incubation) of such antibodies with a biological sample under conditions and for a time sufficient to permit the formation of immunocomplexes.

Detection of the presence of immunocomplexes formed between an antigen described above and an antibody specific for the antigen may be accomplished by a variety of known techniques, such as radioimmunoassays (RIA) and enzyme-linked immunosorbent assays (ELISA). Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods,* E. and S. Livingstone, Edinburgh, 1970); the "western blot" method of Gordon et al. (U.S. Pat. No. 4,452,901); immunoprecipitation of labeled ligand (Brown et al., *J. Biol. Chem.* 255:4980–4983, 1980); enzyne-linked immunosorbent assays as described by, for example, Raines and Ross (*J. Biol. Chem,* 257:5154–5160, 1982); immunocytochernical techniques, including the use of fluorochromes (Brooks et al., *Clin. Exp. Immunol.* 39: 477, 1980); and neutralization of activity (Bowen-Pope et al., *Proc. Natl. Acad. Sci. USA* 81:2396–2400, 1984). In addition to the immunoassays described above, a number of other inununoassays are available, including those described in U.S. Pat. Nos.: 3,817,827; 3,850,752; 3,901,654; 3,935,074; 3,984,533; 3,996,345; 4,034,074; and 4,098,876.

For detection purposes, the antibodies may either be labeled or unlabeled. When unlabeled, the antibodies find use in agglutination assays. In addition, unlabeled antibodies can be used in combination with labeled molecules that are reactive with immrunocomplexes, or in combination with labeled antibodies (second antibodies) that are reactive with the antibody directed against the compound, such as antibodies specific for immunoglobulin. Alternatively, the antibodies can be directly labeled. Where they are labeled, the reporter group can include radioisotopes, fluorophores, enzymes, luminescers, or dye particles. These and other labels are well known in the art and are described, for example, in the following U.S. Pat. Nos.: 3,766,162; 3,791,932; 3,817,837; 3,996,345; and 4,233,402.

In one preferred embodiment for detecting immunocomplexes, a reporter group is bound to the antibody. The step of detecting immunocomplexes involves removing substantially any unbound antibody and then detecting the presence of the reporter group. Unbound antibody is antibody which has not bound to the antigen.

In another preferred embodiment, a reporter group is bound to a second antibody capable of binding to the antibodies specific for the antigen. The step of detecting immunocomplexes involves (a) removing substantially any unbound antibody (i.e., antibody not bound to the antigen), (b) adding the second antibody, (c) removing substantially any unbound second antibody and then (d) detecting the presence of the reporter group. For example, where the antibody specific for the antigen is derived from a mouse, the second antibody is an anti-murine antibody.

In a third preferred embodiment for detecting immunocomplexes, a reporter group is bound to a molecule capable of binding to the immunocomplexes. The step of detecting involv(s (a) adding the molecule, (b) removing substantially any unbound molecule, and then (c) detecting the presence of the reporter group. An example of a molecule capable of binding to the immunocomplexes is protein A.

An alternative to the use of labeled antibodies, labeled second antibodies or labeled molecules reactive with immunuocomplexes generally, is an immunoassay employing a labeled antigen. In such an assay ("indirect" or "competitive"), an antigen present in a sample will compete with labeled antigen for the antibodies.

It will be evident to those of ordinary skill in the art that a variety of methods for detecting immunocomplexes may be employed within the present invention. Reporter groups suitable for use in any of the methods include radioisotopes, fluorosphores, enzymes, luminescers, and dye particles. Further, it will be appreciated that binding partners (other than antibodies) specific for tumor-associated extended type 1 antigens of the present invention may be used to test for such antigens and that complexes formed between such binding partners and antigens may be detected by techniques analogous to those described above for imnmunocomplexes.

The following examples are offered by way of illustration and not by way of limitation.

EXAMPLES

Example 1

HPTLC Immunostaining and Immunoassay with MA$_B$NCC-ST-421 of Neutral Glycolipids Prepared from Tumors and Normal Tissues A. Monoclonal Antibodies and Immunoassays MAb ST-421 was established as previously described (Watanabe et al., *Jpn. J. Cancer Res. (Gann)* 76:43–52, 1985). MAb MNH-1, which defines type 1 chain N-acetyllactosamine (Galβ1→3GlcNAcβ1→R), was prepared in laboratory of the inventors; MAb 1B2, which defines type 2 chain N-acetyllactosamine (Galβ1→4GlcNAcβ1→R), was established as previously described (Young et al., *J. Biol. Chem.* 256:10967–10972, 1981). Anti-Le$^a$ MAb was obtained from Chembiomed Ltd. (Edmonton, Alberta, Canada). Anti-Le$^y$ MAb AH6 was established as previously described (Abe et al., *J. Biol. Chem.* 258:11793–11797, 1983), and did not show any cross-reactivity with Le$^b$. Anti-Le$^b$ MAb was purchased from Chembiomed Ltd. (Edmonton, Alberta, Canada), and showed cross-reactivity with type 1 chain H. Another anti-Le$^b$ MAb was purchased from Monocarb (Lund, Sweden), and showed reactivity with Le$^b$, type 1 chain H, and Le$^y$. HPTLC immunostaining was performed using Whatman HPTLC plates (HP-KF) by a modified version (Kannagi et al., *J. Biol. Chem.* 257:4438–4442, 1982; Kannagi et al., *J. Biol. Chem.* 257:14865–14874, 1982) of the method originally described by Magnani et al. (Magnani et al., *Anal. Biochem.* 109:399–402, 1980).

B. Glycolipid Preparation

All glycolipid samples used were either isolated or synthesized enzmatically. VI$^3$NeuAcnLc$_6$, IV$^3$NeuAcIII$^4$FucLc$_4$, VI$^2$FucnLc$_6$, and IV$^2$FucLc$_4$ were isolated from human placenta, liver adenocarcinoma, human type O erythrocytes, and porcine intestine, respectively, after extraction with IHW (55:25:20) followed by Folch partition, DEAE-Sephadex chromatography, and HPBLC on an latrobeads 6RS-8010 column (Magnani et al., *J. Biol. Chem.* 257:14365–14369, 1982; Watanabe et al., *J. Biol. Chem,* 2548223–8229, 1979; Hakomori et al., *J. Immunol.* 98:31–38, 1967; Stellner et al., *Biochemistry* 12:656–661, 1973). nLc$_6$ and III$^4$FucLc$_4$ were prepared by desialylation of VI$^3$NeuAcnLc$_6$ and IV$^3$NeuAcIII$^4$FucLc$_4$, respectively, by heating the samples at 100° C. for 1 hr in 1% acetic acid. IV$^3$GlcNAcnLc$_4$, IV$_3$Galβ1→3-GlcNAcnLc$_4$, IV$_3$Galβ1→3[Fuc1→4]GlcNAcnLc$_4$ and IV$^3$Galβ1→3[Fuc1→4]GlcNAcIII$^3$FucnLc$_4$ (Le$^a$–Le$^x$) were prepared by enzyatic synthesis. IV$^3$Galβ1→3GlcNAcIII$^3$FucnLc$_4$ was prepared by α-fucosidase treatment of IV$^3$Galβ1→3[Fuc1→4]GlcNAcIII$^3$FucnLc$_4$; i.e., 100 μg of the glycolipid was incubated with 0.2 M citrate buffer (pH 4.5) containing 0.05 units bovine kidney α-L-facosidase (Sigma Chemical Co., St. Louis, Mo.) for 2 hr at 37° C. IV$^2$III$^4$Fuc$_2$Lc$_4$, V$^3$III$^3$Fuc$_2$nLc$_6$, and VI$^2$V$^3$Fuc$_2$nLc$_6$ were prepared biosynthetically by α1→3 fucosylation of IV$^2$FucLc$_4$, nLc$_6$, and VI$^2$FucnLc$_6$ (respectively) as substrates, using α1→3/4 fucosyltransferase from Colo205. α1→3/4 fucosyltransferase was solubilized from Colo205 cells by homogenization in two volumes of 50 mM Hepes buffer (pH 7.0), 0.5 M sucrose, 1 mM EDTA, and 1% Triton CF-54 in a Potter-Elvehjem homogenizer at 4° C. The homogenate was centrifuged at 100,000×g for 1 hr, and the supernatiuat was concentrated to the original volume of cells by dialysis. The enzyme preparation was stored at −80° C. until needed.

Enzymatic α1→3/4 fucosylation was performed in a reaction mixture containing 1 mg glycosphingolipid (GSL) substrate, 1 mg deoxytaurocholate, 10 μmol MnCl$_2$, 25 μmol Hepes buffer (pH 7.0), 5 μmol CDP-choline, 6 μmol GDP-fucose, and 500 μl enzyme preparation in a total volume of 1 ml. The reaction mixture was incubated at 37° C. for 16 hr, then lyophilized, extracted with isopropanol-hexane-water (IHW) (55:25:20) by sonication, and centrifuged. The supernate was subjected to HPLC on an latrobeads 6RS-8010 column using gradient elution of IHW from 55:40:5 to 55:25:20 over 200 min. Two ml fractions were collected and tubes containing the final product were pooled according to HPTLC migration in chloroform-methanol-water 50:40:10. GSL bands were visualized by orcinol spray reagent.

Each GSL with defined structure was characterized by reactivity with specific MAb(s), i.e., Le$^b$/Le$^a$ antigen reacted with anti-Le$^b$ MAbs but not with anti-Le$^y$ MAb AH6; Le$^y$/Le$^x$ reacted with AH6 but not with anti-Le$^b$ nor anti-Le$^x$ MAbs; Le$^a$/Le$^a$ and Le$^a$/Le$^x$ reacted with anti-Le$^a$ MAb as well as with MAb ST-421.

C. TLC Immnunostaining

Figure 1B:
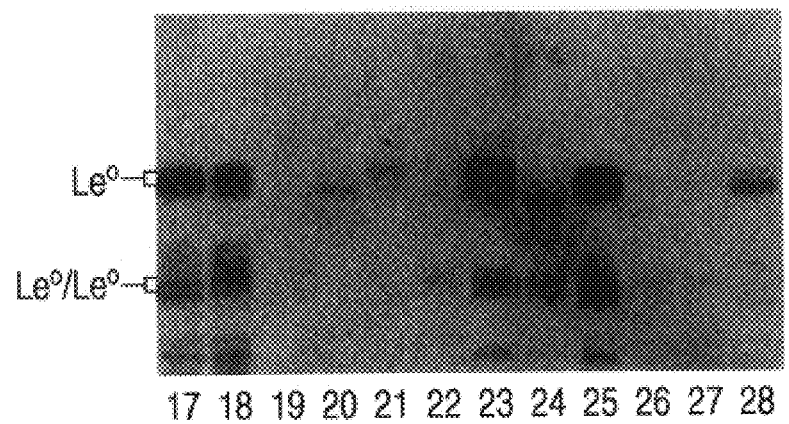
Figure 1C:
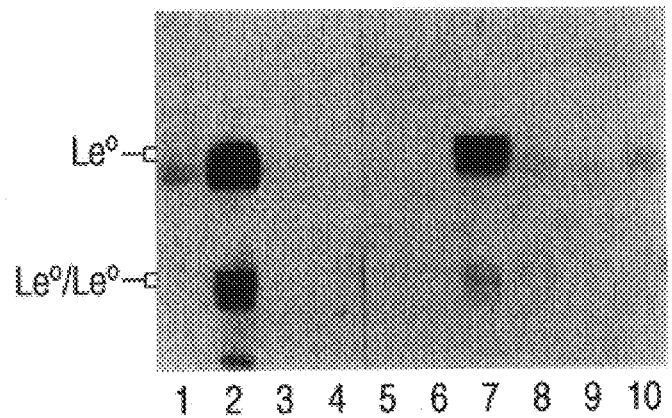

TLC immunostaining of neutral glycolipid fractions prepared from various tumor samples showed the presence of a positive band migrating slower than Le$^a$-active ceramide pentasaccharide, and cross-reacting with anti-Le$^a$ MAb. This band was strongly stained by MAb NCC-ST-421, and was seen in the majority of tumors so far examined. Examples from colonic cancer, breast cancer, Hodgkin's disease, gallbladder cancer, and embryonal rhabdomyosarcoma are shown in FIGS. 1A and 1B. In contrast, no ST-421-positive band was observed in glycolipid fractions prepared from normal tissues such as spleen, liver, kidney, placenta, or lung, with the exception of a positive band from extracts of normal small intestine and pancreas (FIG. 1C). Thus, presence of this slow-migrating, Le$^a$-cross-reactive band is highly limited in normal tissues as compared to cancer tissues. In addition, lanes 3, 5, 10, 17 and 18 (FIGS. 1A and 1B) show a positive band migrating just above the major slow-migrating band. This band may represent an extended Le$^a$ antigen (e.g., Le$^a$ antigen with internal type 1 chain without fucosylation).

D. Reactivity of ST-421 with Dimeric Le$^a$ and Various Related Glycolipids

Figure 7:
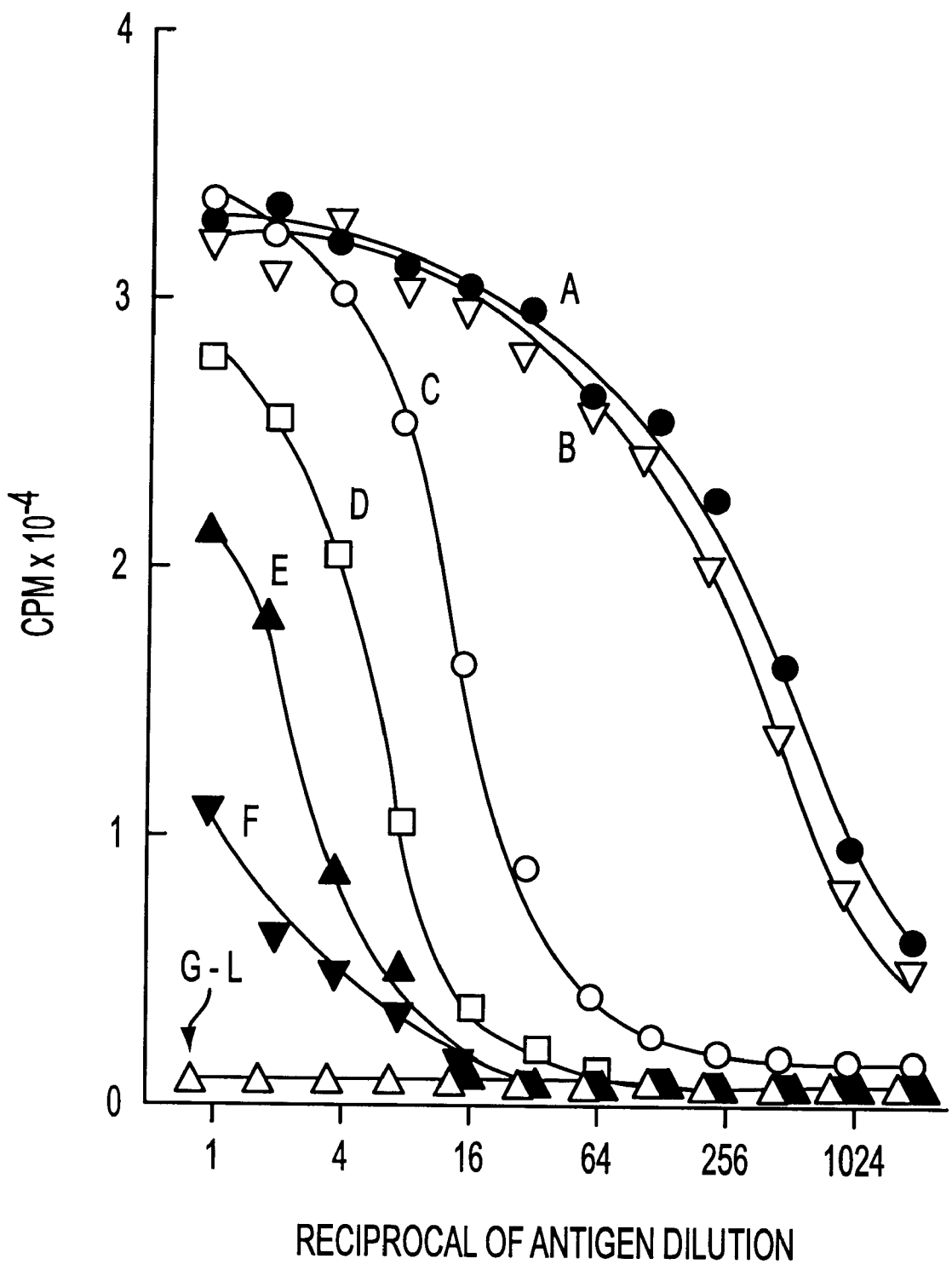
FIG. 7 graphically illustrates the reactivity of dimeric Le$^a$, Le$^a$–Le$^x$ and related glycolipids with MAb NCC-ST-421. Solid-phase radioimmunoassay with MAb ST-421 using serially-diluted dimeric Le$^a$, Le$^a$/Le$^x$, and various structurally-related glycoilpid antigens. Initial concentration of glycolipids was 100 ng. ST421 was used at a concentration of 10 μg/ml. The reactivities of twelve glycolipids (A to L) are shown in this figure, corresponding to various structures shown in Table III (below). A, IV$^3$Galβ1→3[Fucl→4] GlcNAcIII$^3$FucnLc$_4$ (Le$^a$/Le$^x$; structure 10 in Table III); B, V$^4$III$^4$Fuc$_2$Lc$_6$ (dimeric Le$^a$; structure 11); C, IV$^3$Galβ1→3 [Fucα1→4]GlcNAcnLc$_4$ (structure 8); D, III$^4$FucLc$_4$ (structure 1); E, IV$^3$(Galβ1→3GlcNAcIII$^3$FucnLc$_4$ (structure 9); F, V$^3$III$^3$Fuc$_2$nLc$_6$ (structure 7); G, IV$^2$FucLc$_4$ (structure 2); H, IV$^3$Galβ1→3GlcNAcnLc$_4$ (structure 4); I, IV$^2$III$^4$Fuc$_2$Lc$_4$ (structure 3); J, nLc$_6$ (structure 5); K, VI$^2$FucnLc$_6$ (type 2 H with nLc$_6$ core; not shown in Table III); L, VI$^2$V$^3$Fuc$_2$nLc$_6$ (Le$^y$ with nLc$_6$ core; not shown in Table III).

The solid-phase radioimmunoassay as described by Kannagi et al. (*Cancer Res.* 43:4997–5005, 1983) was used. Solid-phase radioimmunoassay using ST-421 showed the strongest reactivity with both dinieric Le$^a$ and the Le$^a$/Le$^x$ hybrid glycolipid (FIG. 7). This antibody could not distinguish between these two antigens, but showed a clear preference for them compared to extended Le$^a$ or simple Le$^a$. Dimeric Le$^x$ and various other structurally related GSLs were not reactive with ST421 (FIG. 7).

Example 2

Isolation of Dimeric Le$^a$ Antigen, Le$^b$–Le$^a$ Antigen and Extended Sialyl Le$^a$ Antigen A. preparation of Tumor Tissue Colo205 cells (ATCC) (Semple et al., *Cancer Res* 38:1345–1355, 1978) were grown in RPMI 1640 medium containing 10% fetal calf serum. Cells were harvested and passed approximately every 7 days. Cells harvested were trypsinized, centrifuged, washed twice with phosphate-buffered saline (pH 7.4) and counted using a hemocytometer. 4×10$^6$ cells mere injected subcutaneously into each of 6 athymic (nude) mnice. Tumors (approximately 2 ml each) were excised after 2 weeks and stored frozen at −80° C. until needed.

B. Isolation of the Slow-Migrating. Le$^a$-Active Component (Dimeric Le$^a$) from Colo205 Tumor Approximately 200 g of tumors were extracted with isopropanol-hexane-water (IHW) (55:25:20) followed by Folch partition, DEAE-sephadex chromatography and HPLC on an Iatrobeads 6RS-8010 column. Gradient elution of the upper-phase neutral fraction was performed in IHW from 55:40:5 to 55:25:20 over 200 minutes. Two-ml fractions were collected and pooled according to HPTLC migration in chloroform-methanol-water (50:40:10). The slow-migrating Le$^a$-active fraction (revealed by TLC imunostaining) was further purified by preparative TLC on Merck HPTLC plates (Silica Gel 60, Merck, Darmstadt, Germany) and used for structural characterization.

C. Isolation of Le$^b$–Le$^a$ Antigen

A positive band (by immunostaining with MAb NCC-ST-421 according to Example 1) which migrates just below diferic Le$^a$ antigen was purified using the methods described in section B above.

D. Isolation of Extended Sialyl-Le$^a$ (or SLe$^a$–Le$^a$)

Examination of monosialo-ganglioside fraction of Colo 205 cells led to isolation or resulted in isolation of one major ganglioside by a high performance thin layer chromatography technique. The major band was extracted and characterized. The structure was identified as:

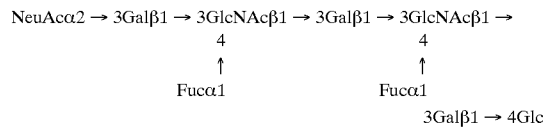

Figure 13:
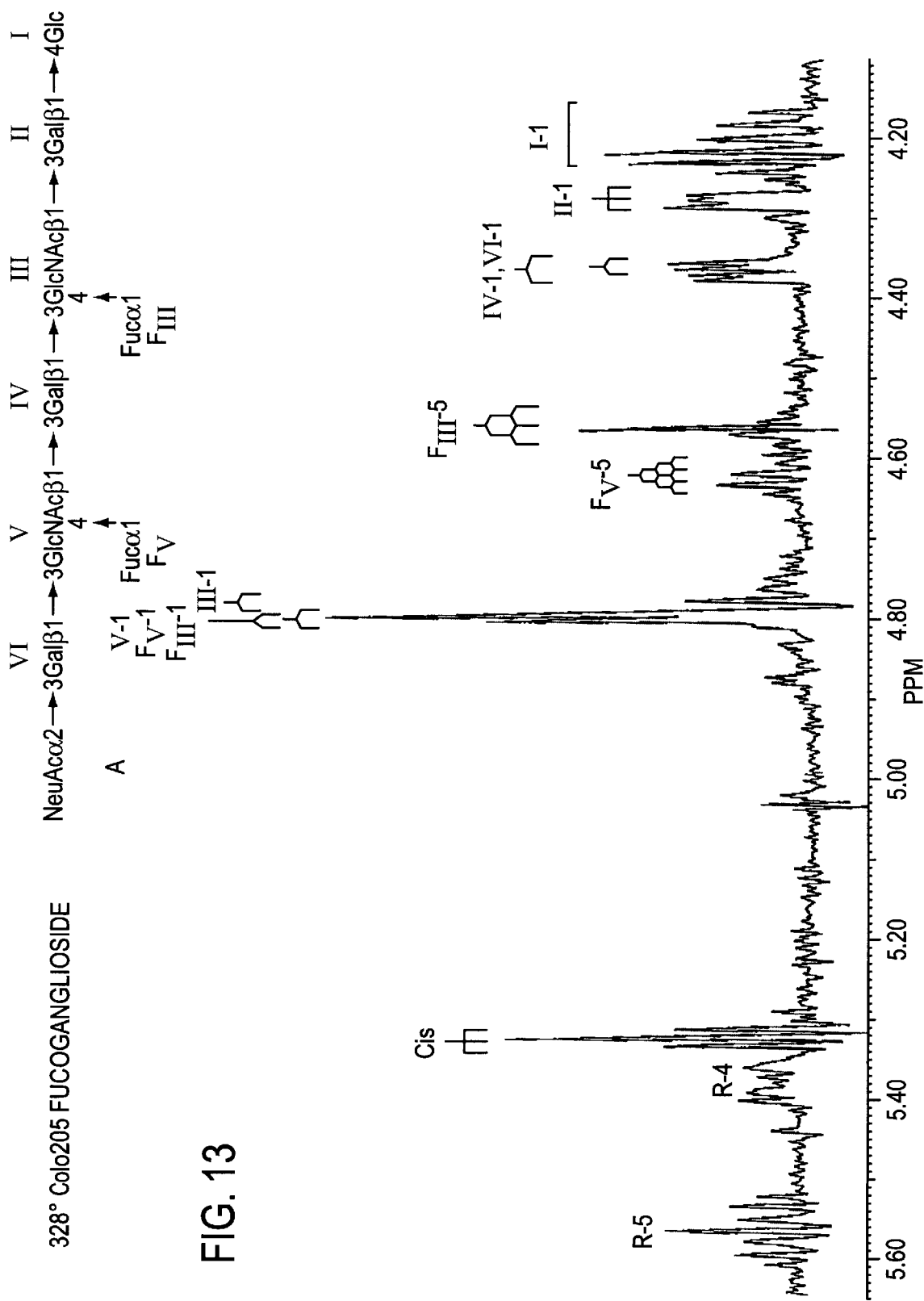
FIG. 13 is the $^1$H-NMR spectrum of extended sialyl Le$^a$ from chemical shift at 4.20 ppm to 5.60 ppm covering sugar I(Glc), II(Gal), III(GlcNAc), IV(Gal), V(GlcNAc) and VI(Gal as well as fucose linked to III GlcNAc identified as F$_{III}$ and fucose linked to V GlcNAc as indicated by F$_{IV}$. In this spectrum, all anomeric proton spectrums of F$_V$ and F$_{III}$ are indicated as F$_V$-1 and F$_{III}$-1. In addition, spectrum C5 proton of fucoses are indicated by multiple coupling as indicated by F$_{III}$-5 and F$_V$-5. Spectrum marked as Cis is a Cis double bond of sphingosine and R-5 and R-4 indicate spectrum of sphingosine.
Figure 14:
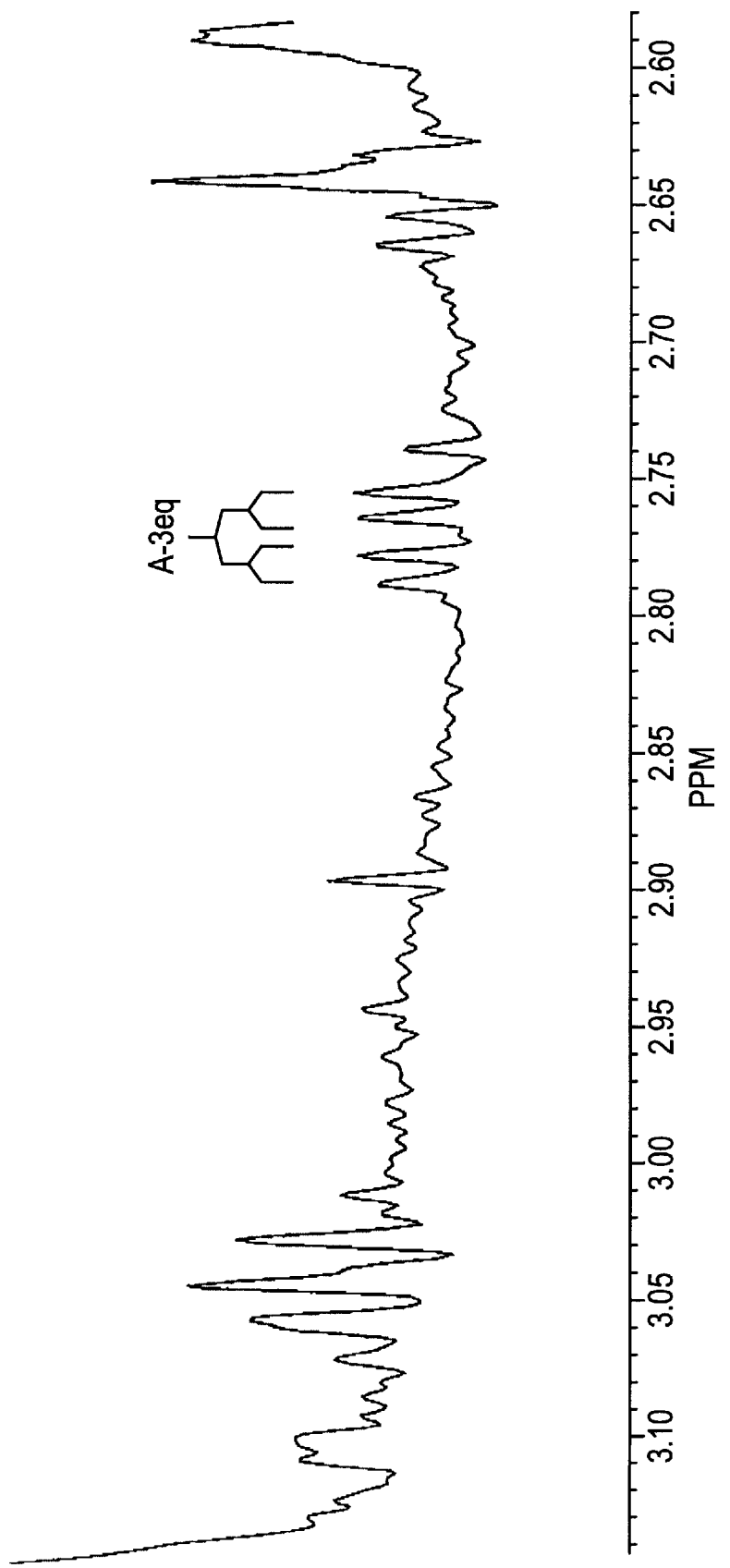
FIG. 14 is a typical $^1$H-NMR spectrum for thiree equatorial protons of sialic acid of extended sialyl Le$^a$.
Figure 15:
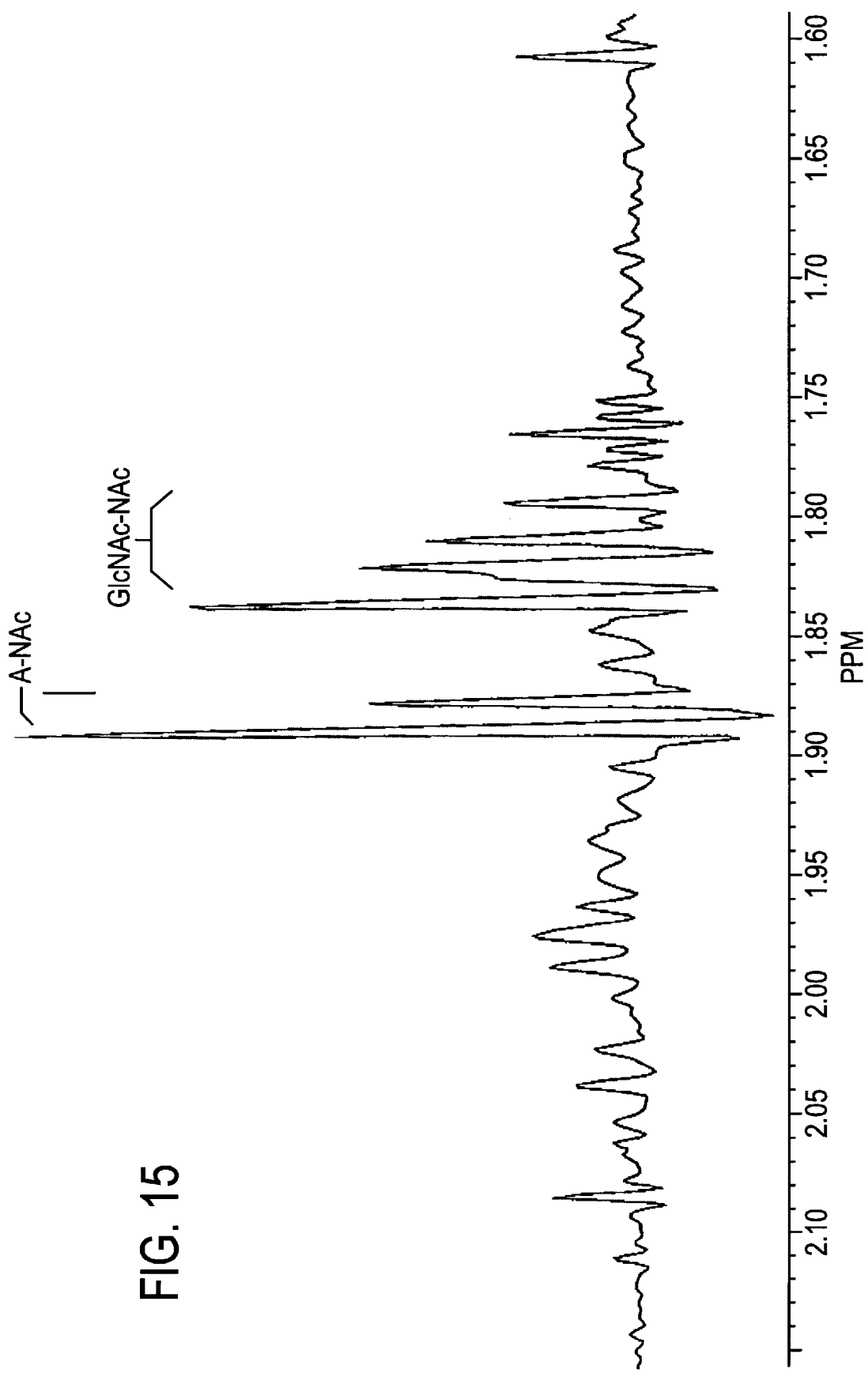
FIG. 15 is the $^1$H-NMR spectrum of extended sizilyl Le$^a$ and shows two major spectrums for the N-acetyl group of sialic acid marked as A-NAc. In addition, this figure also shows the spectrum of the N-acetyl group of GlcNAc marked as GlcNAc-NAc.

This structure was verified by $^1$H-NMR spectroscopy as shown in FIGS. 13, 14 and 15.

Example 3

Characterization of Dimeric Le$^a$ and Le$^b$–Le$^a$ Antigens

A. Enzymatic Degradation

Enzymatic degradation of 1 mg dimeric Le$^a$ was performed by sequential hydrolysis with 0.5 units of α-fucosidase (bovine kidney), 0.5 units of β-galactosidase (Cackbean), and 0.5 units of β-N-acetylglucosaminidase (bovine epididymis) (Sigma Chemical Co., St. Louis, Mo.). All reactions were carried out in 0.2 M sodium citrate (pH 4.5) for 4 hr at 37° C. in a water bath with shaking. Purification of each degradative product was performed by preparative HPTLC.

Figure 2A:
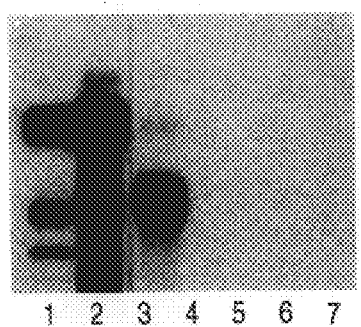
FIG. 2 shows the results of TLC immunostaining of dimeric Le$^a$ after successive enzymatic degradation. Panel A TLC immrunostaining pattern with anti-Le$^a$ MAb; Panel B, TLC immunostaining with MAb MNH-1; Panel C, TLC immunostaining with MAb 1B2. Lane 1, type "O" erythrocyte upper neutral fraction; lane 2, Colo205 upper neutral glycolipid fraction; lane 3, dimeric Le$^a$; lane 4, slow-migrating band "b" after α-fucosidase treatment of dimeric Le$^a$; lane 5, fast-migrating band "a" after continued α-fucosidase treatment of dimeric Le$^a$; lane 6, product formed after β-N-acetylhexosaminidase treatment of lane 5 compound; lane 7, product formed after β-galactosidase treatment of lane 6 compound.
Figure 2B:
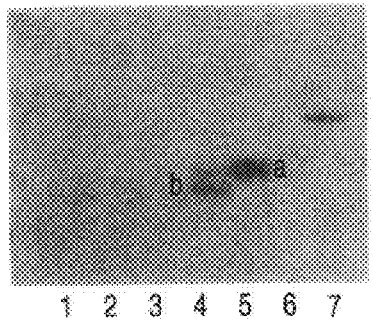
Figure 2C:
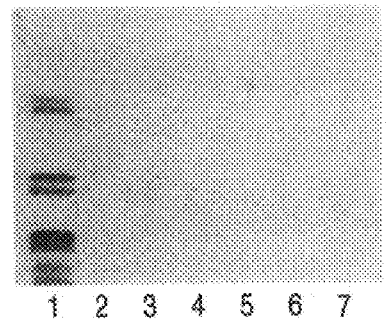

TLC immunostaining of the purified antigen component with various MAbs was performed before and after successive enzymatic degradation. Treatment of the component with bovine kidney a-fucosidase resulted in two bands: a fast-migrating band "a" (FIG. 2, lane 5), and a slow-migrating band "b" (FIG. 2, lane 4), both of which reacted with MAb MNH-1[3] (FIG. 2B) but not with anti-Le$^a$ or 1B2 (FIGS. 2A, 2C). Extensive treatment of the original antigen with bovine kidney α-fucosidase resulted in decreased band b and increased band a. Bands a and b are therefore assumed to be Lc$_6$ (Table III, structure 6) and III$^4$FucLc$_6$ (structure 13), respectively, based on their reactivity with MAbs and on further enzymatic degradation patterns. Since MNH-1 reacts specifically with unsubstituted type 1 chain structure (Galβ1→3GlcNAcβ1→3Gal-β1→R), and MAb 1B2 reacts with unsubstituted type 2 chain (Galβ1→4GlcNAcβ1→3Gal-β1→R), no type 2 chain stru (cture could be present at the terminus. Therefore, treatment of the antigen with bovine kidney α-fucosidase resulted in removal of the fucose linked at the peniltimate V-GlcNAc residue, which precedes removal of the fucose residue linked at the internal (III-GlcNAc) residue.

Jackbean β-galactosidase treatment of the fucosidase-treated product (corresponding to band a) resulted in loss of reactivity with MAb MNH-1 (FIGS. 2B, lane 6) and produced a band migrating higher than the α-fucosidase-treated material. This component (i.e., product after treatment with α-fucosidase and β-galactosidase) did not react with MAbs MNH-1, 1B2, or ST421, and was further degraded with β-N-acetylglucosaminidase from bovine epididymis. The product showing TLC migration corresponding to Lc$_4$ reacted strongly with MAb MNH-1 (FIG. 2B, lane 7) but did not react with MAb 1B2 (FIG. 2C, lane 7). These results indicate strongly that not only the terminal but also the internal carbohydrate core of this glycolipid antigen consists of type 1 chain, i.e., extended type 1 structure which is α1→fucosylated at the penultimate as well as the internal GlcNAc residue. The structure is assumed to be dimeric Le$^a$ (Table III, structure 11). This assumption was further confirmed by $^+$FAB-MS, $^1$H-NMR, and methylation analysis as described in sections B, C and D below.

Extended sialyl-Le$^a$ on the SLe$^a$–Le$^a$ structure was verified by enzymatic degradation with sialidase to yield the same compournd as Le$^a$–Le$^a$ as verified by thin layer chromatography as well as immunostaining with monoclonal antibody ST-421. The original sialyl Le$^a$–Le$^a$ or extended Le$^a$ do not show any reactivity with MAb ST-421. However, this compound showed reactivity with MAb directed to sialyl-Le$^a$ such as N-19-9, NKH-1 and NKH-2.

B. $^1$H-NMR Spectroscopy

Approximately 1 mg of sample (from Example 2.B.) was deuterium exchanged by repeated lyophilization from DMSO-d$_6$/D$_2$O (98:2), then dissolved in 0.4 ml of this solvent for $^1$H-NMR analysis. One-dimensional spectra were recorded at 308 and 328±2°K. on a Bruker (Karlsruhe, West Germany) AM-500 Fourier transform spectrometer/ Aspect 3000 data system, using quadrature detection. The sweep width was 5000 Hz, collected over 16K data points. The residual HOD resonance was suppressed using a pre-saturation pulse during the preparatory delay (PD) period. The PD was 2.0 sec. A Lorentzian to Gaussian transformation was used for resolution enhancement.

Figure 3:
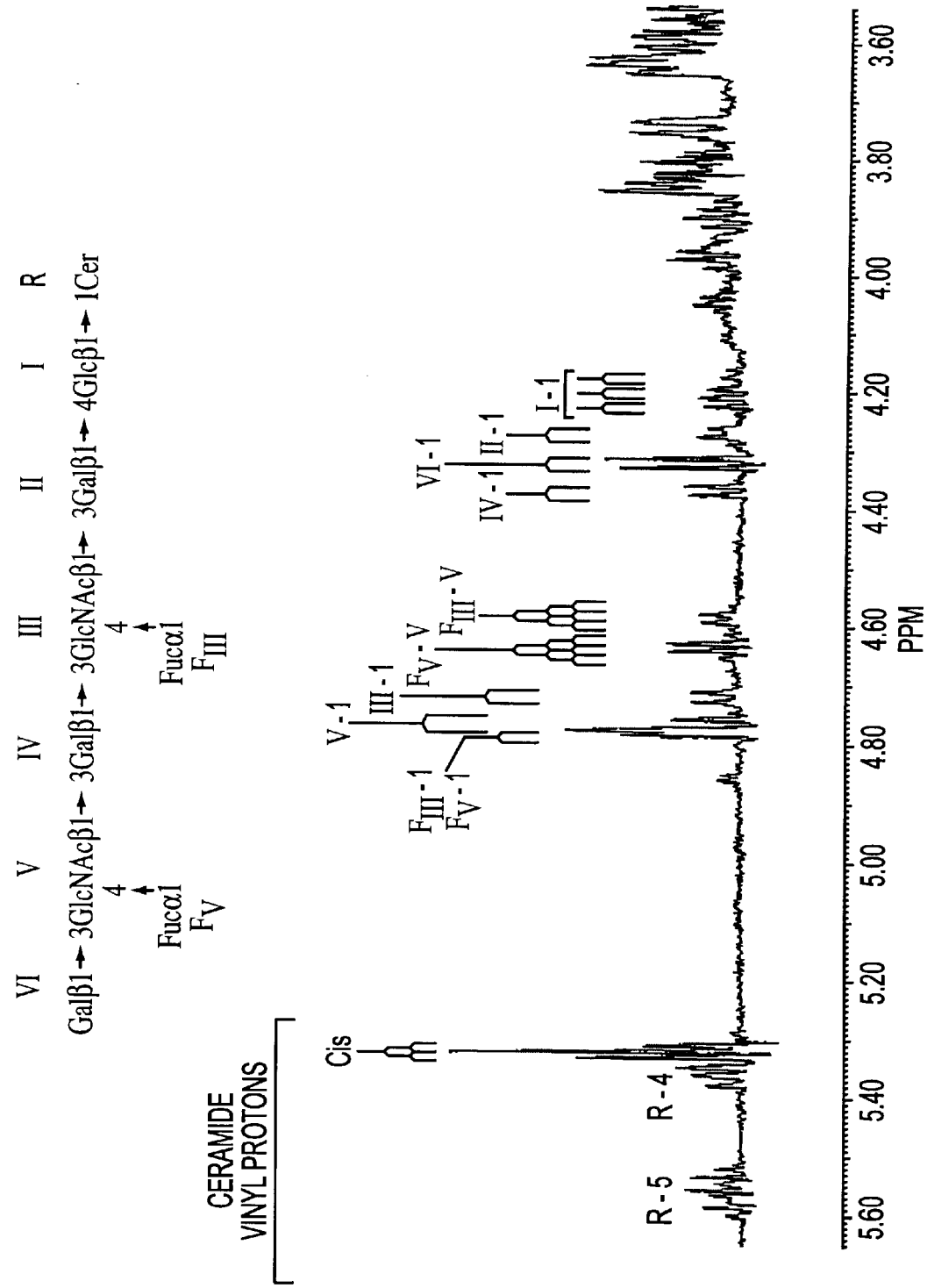
FIG. 3 depicts a resolution-enhanced 1-D $^1$H-NMR spectrum of dimeric Le$^a$ (downfield region). Arabic numerals refer to ring protons of residues designated by roman numerals in the corresponding structure shown at top of figure. R refers to protons of the sphingosine backbone only; Cis refers to vinyl protons of unsaturated fatty acids. Fuc H-5/CH$_3$ connectivities were confirmed by decoupling.

The downfield portion of the 1-D $^1$H-NMR spectrum of the slow-migrating Le$^a$-active GSL, obtained in DMSO-d$_6$/ 2% D$_2$O at 308°K., is reproduced in FIG. 3. Overall, the spectrum was characterized by a high degree of correlation of resonances with those previously published for Le$^a$-pentaglycosylceramides (Dabrowski et al., Arch. Biochem. Biophys. 210:405–411, 1981) (allowing for temperature differences), particularly for sets of α-Fuc H-1, H-5, and CH$_3$ resonances, which are known to be particularly reliable structural reporter groups. It is worth noting that the presence of a small amount (5%–10%) of type 2 chain structures was indicated by the α-anomeric resonance at ≈4.85 ppm (≈4.88 ppm at 328°K.), which is diagnostic for H-1 of Fucα↑3 groups in GSLs bearing one or more Le$^x$-haptens as a minor impurity (Levery et al., Carbohydr. Res. 151:311–328, 1986; Levery et al., Carbohydr. Res. 178:121–144, 1988; Hakomori et al., J. Biol. Chem. 259:4672–4680, 1984). For the major component, it was found that satisfactory assignments of glycosyl H-1, and fucosyl H-5 and CH$_3$, resonances could be made based on the hypothesis that the GSLs consisted of a repeating type 1 chain (→3Galβ1→3GlcNAcβ1→) unit, with Fucα→4 to GlcNAc groups attached, creating a dimeric Le$^a$ structure.

The structure and resonance assignments were made according to the following arguinents.

In the spectrum of this GSL (FIG. 3), a set of downfield saccharide resonances were found at chemical shifts virtually identical to those found in the terminal trisaccharide of Le$^a$ (Dabrotvski etal., *Arch. Biochem. Biophys.* 210:405–411, 1981): β-Gal H-1 at 4.321 ppm ($^3J_{1,2}$=7.3 Hz); β-GlcNAc H-1 at 4.768 ppm ($^3J_{1,2}$=8.5 Hz); α-Fuc H-1 at 4.781 ppm ($^3J_{1,2}$=3.7 Hz). The remaining saccharide H-1 resonances were consistent with an internal Le$^a$-pentaglycosylceramide (Dabrowski et al., *Arch. Biochem. Biophys.* 210:405–411, 1981), provided one assumes a downfield shift of β-Gal IV-1 (δ≈0.05 ppm), and an upfield shift of III-1 (δ≈0.05 ppm), on attachment, to O-3 of Gal IV, of the terminal Le$^a$-trisaccharide hapten. The former effect, a glycosylation-induced downfield shift, is generally observed upon chain elongation, whereas assumption of the latter, a remote shift effect, requires some rationalization based on a knowledge of secondary structure. Two α-Fuc H-5 resonances, coupled to upfield CH$_3$ doublets ($^3J_{5,6}$=6.7 Hz), were found in the spectrum one at a chemical shift virtually identical to that found in the spectrum of Le$^a$ (4.585 ppm), the other shifted somewhat downfield (4.636 ppm). Interestinglv, the α-Fuc H-1 resonances occur at virtually identical chemical shifts, sinilar to the case with Fucα1→3GlcNAc substituents on repeating type 2 chain (Le$^x$) structures (Levery et al., *Carbohydr. Res.* 151:311–328, 1986; Levery et al., *Carbohydr. Res.* 178:121–144, 1988).

According to this analysis, H-5 of the internal Fucα→4 group is in a chemical environment similar to that in Le$^a$-pentaglycosylceramide, while that of the outer Fucα1→4 is deshielded. This is in contrast to the α-Fuc H-1 resonances, which are identical, or to the β-GlcNAc H-1 resonances, where that belonging to the innermost saccharide is shifted upfield relative to its position in Le$^a$, while that of the outermost GlcNAc occurs at shifts identical to that in Le$^a$. Analogous examples of long-range "cross-talk" were observed in repeating type 2 Le$^x$-hapten structures (Levery et al., *Carbohydr. Res.* 151:311–328, 1986; Levery et al., *Carbohydr. Res,* 18:121–144, 1988), and presumably give clues to secondary structural interactions between consecutive haptenic units, although these may be due to the through-space shielding or deshielding effects of anisotropic groups on saccharides that are not necessarily in steric contact.

The proposed structural and resonance assignments are summarized in FIG. 3 and Table I. The structure was further confirmed by 2-D $^1$H-NMR experiments, as well as by linkage analysis, by GC-MS, and FAB-MS analysis of the permethylated GSLs as described below.

C. Methylation Analysis

The remainder of the permethylated sample was hydrolyzed, reduced, and acetylated according to published procedures (Levery and Hakomori, *Meth. Enzymol.* 138:13–25, 1987). GC-MS analysis of partially methylated alditol acetates (PMAAs) was perfomed using a 30m DB-5 (0.25 μm i.d.) bonded phase fused silica capillary column as previously described (Clausen et al., *J. Biol. Chem.* 262:14228–14234, 1987; Ostrander et al., *J. Biol. Chem.* 263:18716–18725, 1988; Nudelman et al., *J. Biol. Chem.* 263:13942–13951, 1988).

Figure 4:
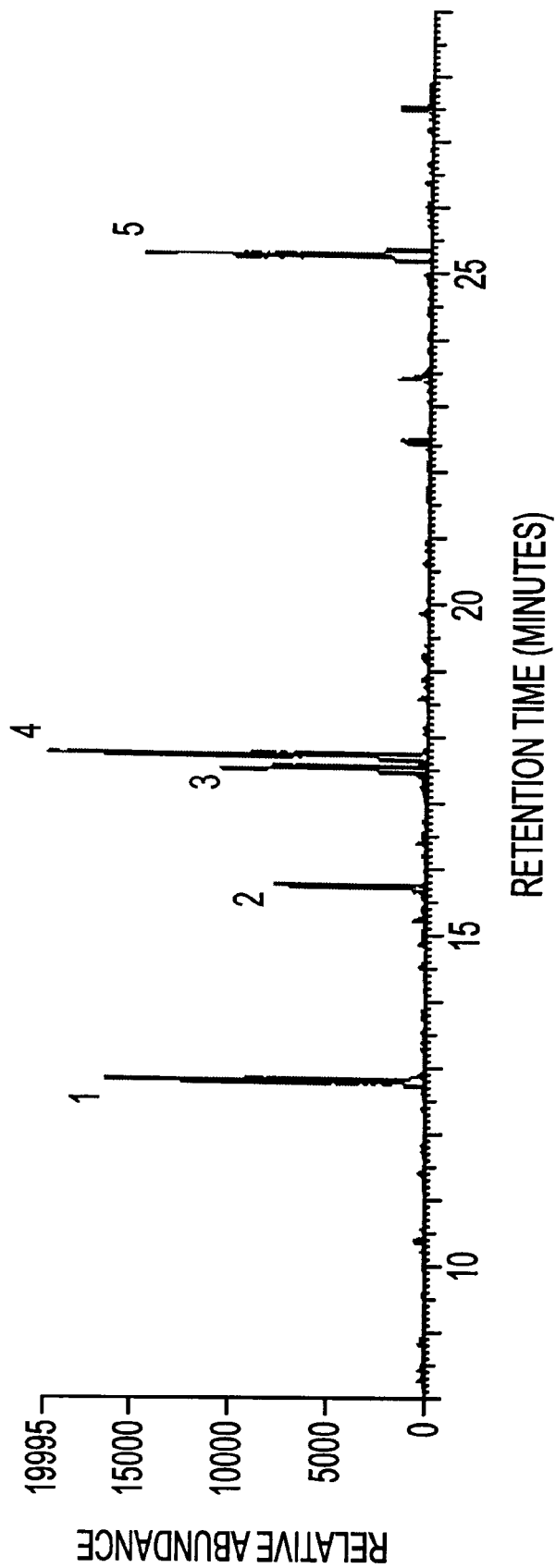
FIG. 4 depicts chemical ionizationa mass chromatograms of partially methylated alditol or hexosaminitol acetates yielded from permethylated Colo205 glycolipid antigen. Separation was performed on a DB-5 bonded phase fused silica column. Peaks identified were (1) 2,3,4-tri-O-Me-Fuc-, (2) 2,3,4,6-tetra-O-Me-Gal-, (3) 2,3,6-tri-O-Me-Glc-, (4) 2,4,6-tri-O-Me-Gal-, (5) 6-mono-O-Me-GlcNAcMe. Chromatograms are summations of all relevant MH+, (MH-32)+, and (MH-60)+ ions.

Linkage analysis was carried out on the putative dimeric Le$^a$ GSL by capillary GC-chemical ionization MS, using the bonded stationary phase DB-5. PMAAs of 2,3,4-tri-O-Me-Fuc (terminal Fuc); 2,3,4,6-tetra-O-Me-Gal (terminal Gal); 2,3,6-tri-O-Me-Glc (4-linked GLC); 2,4,6-tri-O-Me-Gal (3-linked Gal); and 6-mono-O-Me-GlcNAcMe (3,4-linked GlcNAc) were clearly identified. These were present in an approximate ratio of 2:1:1:2:2 (FIG. 4). A small trace of 3,6-di-O-Me-GlcNAcMe (1%–2% of 6-mono-peak), probably arising from unsubstituted type 2 core chain contaminants, was observed. This analysis was consistent with the proposed structure of dimeric Le$^a$, although it would obviously be impossible to differentiate results for the Le$^a$-hapten from those for the isomeric Le$^x$-hapten, since these produce identical mono-O-Me-GlcNAcMe derivatives. However, the NMR analysis clearly showed that the Le$^x$-structure is present only as a minor contaminant in this fraction.

D. $^+$FAB-MS

A sample of the glycolipid (≈50 μg) was permethylated by the method of Ciucanu and Kerek (Ciucanu and Kerek, *Carbohydr. Res.* 131:209–217, 1984), as modified by Larson et al. (Larson et al., *Carbohydr. Res.* 161:281–290, 1987), except that equal volumes of MeI and DMSO were used (200 μl each). The reaction time was 60 min and MeI was removed by flushing with N$_2$ for 25 min at 37° C. prior to partitioning between CHCl$_3$ and H$_2$O. After washing 3× with H$_2$O, the CHCl$_3$ was dried under N$_2$, and a portion of the permethylated sample was subjected to $^+$FAB-MS, performed on a JEOL (Tokyo, Japan) HX-110/DA-5000 mass spectrometer/data system. Aliquots of permethylated sample (≈20 μg) in MeOH were transferred to a FAB target and suspended in 3-nitrobenzyl alcohol matrix (Meili and Seibl, *Org. Mass Spectrom.* 19:581–582, 1984; Barber et al., *Rapid Commun. Mass Spectrom.* 2:18–21, 1988) with and without 15-Crown-5 (Holmes and Levery, *Arch. Biochem. Biophys.* 274:633–647, 1989; Isobe et al., *Trends Anal. Chem* 6:78–81, 1987; Holmes, *Arch. Biochem. Biophys.* 270:630–646, 1989). Additional experiments were performed with addition of sodium acetate to matrix (Egge and Peter-Katalinic, *Mass Spectrom. Rev.* 6:331–393, 1987; Dell, *Adv. Carbohydr. Chem. Biochem.* 45:19–72, 1987). Scan range was 100–3000 a.m.u.; scan slope 1 min 30 sec; acceleration voltage 10 kV; resolution 3000; xenon beam, 6 kV. Three scans were accumulated for each spectrum KI/CsI was used as calibration standard.

Figure 5A:
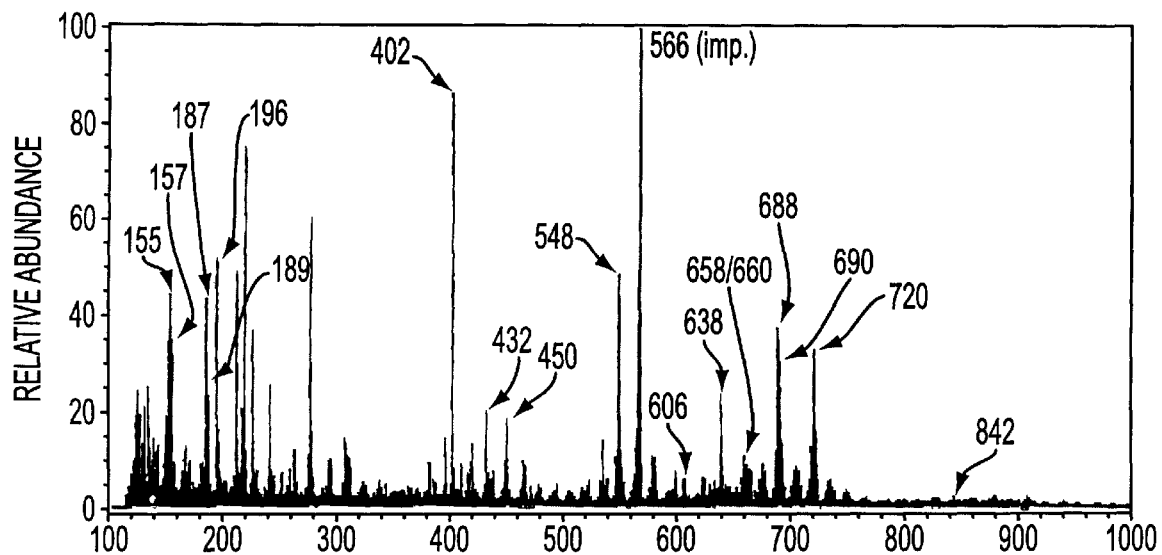
FIG. 5 depicts a positive ion fast atom bombardment mass spectrum of permethylated dimeric Le$^a$. The figure is a composite of three acquisitions optimized for sensitivity under different conditions. Segment from 100–1800 a.m.u. was acquired with NBA only as matrix. Lower segment from 1800–2500 a.m.u. was acquired with addition of 15-Crown-5 to matrix. Insert segment (1900–2500 a.m.u.) was acquired with addition of sodium acetate to matrix. All assignments are nominal monoisotopic masses.
Figure 5B:
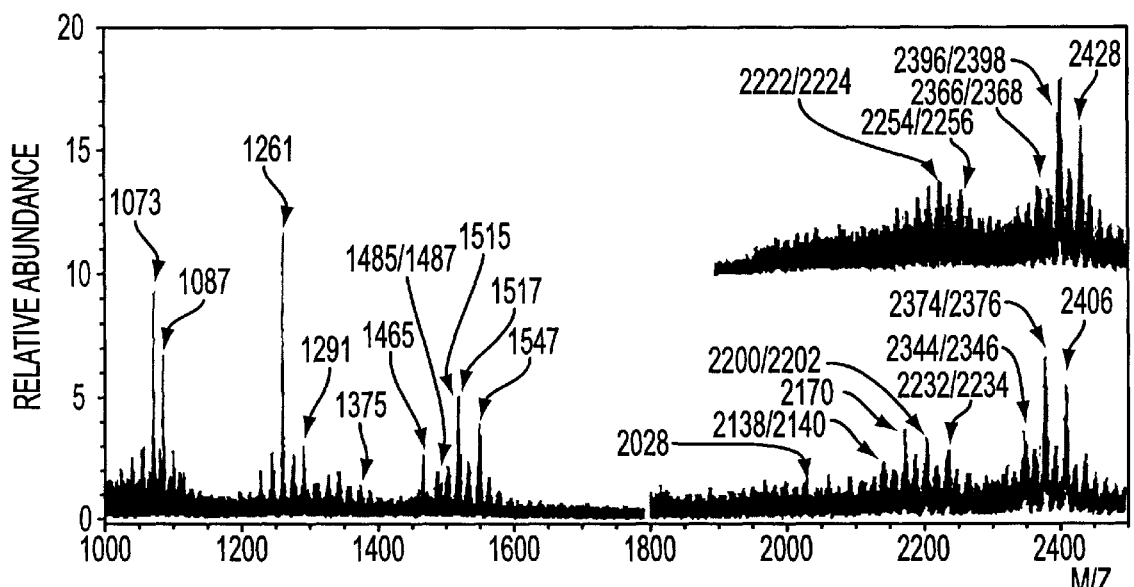

Following permethylation, the GSL was analyzed by FAB-MS in the positive ion mode (FIG. 5). The predominant pseudomolecular ions observed (MH$^+$, nominal masses of 2374, 2376, and 2406 a.m.u.) were consistent with the composition deoxy-Hex$_2$.Hex$_4$.HexNAc$_2$ plus ceramides consisting of sphingosine/fatty acid combinations dl8:1/h24:1, d18:1/h24:0, and tl8:0/h24:1, respectively. Less abundant pseudomolecular ions corresponding to other ceramide compositions were also observed (see Table II). A consistent set of ceramide fragments (m/z 688, 690, 720, etc.) were found in the lower mass end of the spectrum (FIG. 5, Table II). An additional set of less abundant pseudomolecular ions (predominantly at 2200, 2202, and 2232 a-mi.) corresponded to an impurity with the composition deoxyHex.Hex$_4$.HexNAc$_2$ in combination with the same ceramide moieties. The identification of all pseudomolecular ion species was confirmed by addition of NaAc to the FAB matrix, which produced a mass shift of 22 a.m.u. for each (see inset, FIG. 5, Table II).

Figure 6:
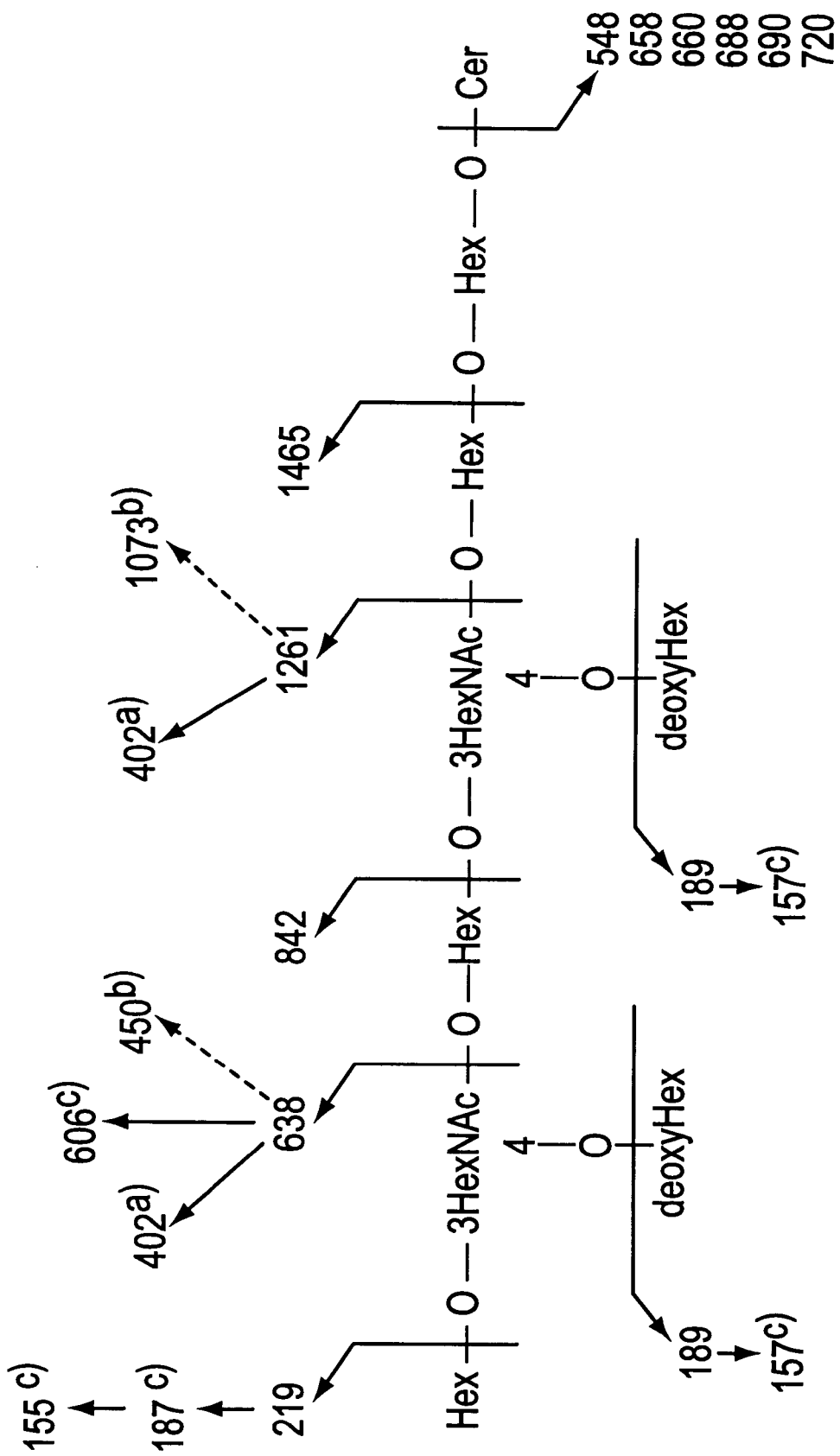
FIG. 6 depicts a proposed scheme for fragmentation of permethylated dimeric Le$^a$. All fragments are assigned nominal, monoisotopic masses. Pseudomolecular ions and additional fragments are listed in Table II.

A number of sequence-related A$_1$-type fragments, produced by cleavage at glycosyl linkages with charge retention of the non-reducing portions (Egge and Peter-Katalinic, *Mass Spectrom. Rev.* 6:331–393, 1987; Dell, *Adv. Carbohydr. Chem. Biochem.* 45:19–72, 1987), were observed in high abundance. Key fragments, consistent with the proposed dimeric Le$^a$ structure, were found at m/z 638 and 1261, representing deoxyHex.Hex.HexNAc and deoxyHex$_2$.Hex$_2$.HexNAc$_2$, respectively (see FIG. 6). Of particular significance was the secondary fragment at m/z 402, produced by neutral loss of the 3-substituents from N-acetylhexosaminyl residues at the non-reducing ends of both of the major primary fragments (i.e., 638-HexOH and 1261-deoxyHex.Hex.Hex.NAc.HexOH) (Egge and Peter-Kataliic, *Mass Spectrom. Rev.* 6:331–393, 1987; Dell, *Adv. Carbohydr. Chem. Biochem.* 45:19–72, 1987). These are consistent with the Galβ1→3GlcNAc linkages of type 1 chain repeating core units. In the +FAB mass spectrum of the isometric repeating type 2 chain dimeric Le$^x$ structure, the abundant loss of the 3-liinked Fuc residues as deoxyHexOH produces major fragments at m/z 432 and 1055, as reported previously (Holmes and Levery, *Arch. Biochem. Biophys.* 24:633–647, 1989). Another key difference from the mass spectrum of dimeric Le$^x$ was the abundant group of ceramide-containing fragments at m/z 1375, 1515, 1517, and 1547. These must be produced by neutral loss of the 3-linked substituent from the internal HexNAc residue of the pseudomolecular ions (MH-deoxyHex.Hex.HexNAc.HexOH). An additional fragment at m/z 1073 is believed to result from β-cleavage (Dell, *Adv. Carbohydr. Chem. Biochem.* 45:19–72, 1987) of a 4-linked Fuc residue from the primary fragment at m/z 1261 (1261−189+1).

The group of ceramide-containing fragments observed primarily at m/z 2028, 2140, 2170, and 2200 (overlapping with the monofucosyl MH+cluster) appeared to result from uniform loss of 206 a.m.u. from the difucosyl MH+ions. Since this is seemingly consistent with loss of deoxyHexOH from the difucosyl MH+ions, it could be taken as an indication of sonle impurity of type 2 chain structure losing 3-linked Fuc as a neutral fragment. However, the relative abundance is inconsistent with the small quantity of type 2 chain Le$^x$ observed in the $^1$H-NMR spectrum. Moreover, these fragments were not observed in such abundance even from the pseudomolecular ions of pure permethylated dimeric Le$^x$ under similar conditions (Holmes and Levery, *Arch. Biochem. Biophys.* 274:633–647, 1989). Thus, it is unclear at this time why they are produced in this spectrum, in seeming contradiction to previous observations of preferred neutral loss of 3-linked substituents on HexNAc. It may be related to an unusual steric condition peculiar to the repeating dimeric Le$^a$ structure.

Finally, fragments at m/z 1087 and 1291 were consistent with the presence of some monofucosylated impurity. Similar fragments were observed in the spectrum of an isomeric synthetic monofucosyl type 2 chain structure (Holmes and Levery, *Arch. Biochem. Biophs.* 274:633–647, 1989). However, the relatively low abundance of ion at m/z 464 (Hex.HexNAc) indicates that, in this case, the single deoxyHex residue must be attached primarily to the subterminal, rather than internal, HexNAc.

E. Le$^b$–Le$^a$ Antigen

The structure of the isolated Le$^b$–Le$^a$ antigen was confirmed using the analytical techniques described in sections A–D above.

TABLE I

Chemical shifts (ppm from tetramethylsilane) and $^3J_{1,2}$ coupling constants (Hz) of glycosyl H-1 resonances[a] for the slow-migrating Le$^a$-active GSL in dimethylsulfoxide-d$_6$ at 308° K. and 328° K.

| T (° K.) | Galβ1 —————→3GlcNAcβ1—→3Galβ1—————→ 3GlcNAcβ1—→ 3Galβ1—→ 4Glcβ1—→1Cer | | | | | | | |
| --- | --- | --- | --- | --- | --- | --- | --- | --- |
| | Fucα——→ 4 | | | Fucα——→ 4 | | | | |
| 308° | 4.321(7.3) | 4.781(3.7) | 4.768(8.5) | 4.366(7.3) | 4.781(3.7) | 4.722(7.9) | 4.269(6.7) | 4.203(7.3) |
| 328° | 4.341(7.3) | 4.799(3.7) | 4.800(7.9) | 4.382(7.3) | 4.799(3.7) | 4.770(7.9) | 4.284(7.3) | 4.208(7.9) |

[a]Additional resonances were found as follows: A) at 308° K., α-Fuc F$_{III}$-5, 4.585 ppm; F$_V$-5, 4.636 ppm; F$_{III}$-6 (CH$_3$), 1.001 ppm; F$_V$-6 (CH$_3$), 1.006 ppm; β-GlcNAc NAc, 1,816 and 1.834 ppm; B) for 328° K., α-Fuc F$_{III}$-5, 4.544 ppm; F$_V$-5, 4.589 ppm; F$_{III}$-6 (CH$_3$), 1.019 ppm; F$_V$-6 (CH$_3$), 1.024 ppm; β-GlcNAc NAc, 1.824 and 1.841 ppm; all α-Fuc = $^3J_{5,6}$ = 6.7 Hz.

TABLE II

Nominal masses (a.m.u.) calculated for major ceramide-containing ions in the +FAB mass spectrum of permethylated dimeric Le$^a$ glycosphingolipid from Colo205 cells.

| sphingosine | fatty acid | Cer+ | MH+ | [MH-R$_1$[a]]+ | [MH-R$_2$[b]]+ | MNa+ | MH+ (monofuc)[c] | MNa+ (monofuc) |
| --- | --- | --- | --- | --- | --- | --- | --- | --- |
| d18:1 | 16:0 | 548 | 2234 | 2028 | 1375 | 2256 | 2060 | 2082 |
| d18:1 | 24:1 | 658 | 2344 | 2138 | 1485 | 2366 | 2170 | 2192 |
| d18:1 | 24:0 | 660 | 2346 | 2140 | 1487 | 2368 | 2172 | 2194 |
| d18:1 | h24:1 | 688 | 2374 | 2168 | 1515 | 2396 | 2200 | 2222 |
| d18:1 | h24:0 | 690 | 2376 | 2170 | 1517 | 2398 | 2202 | 2224 |
| t18:0 | h24:1 | 720 | 2406 | 2200 | 1547 | 2428 | 2232 | 2254 |

[a]R$_1$ = deoxyHexOH
[b]R$_2$ = deoxyHex.Hex.HexNAc.HexOH
[c]monofuc = monofucosylated impurity

TABLE III

Structures of glycolipids with fucosylated lacto-series type 1 and type 2 chain.

1. III$^4$FucLc$_4$ (Le$^a$ penta)

$$Gal\beta1 \rightarrow 3GlcNAc\beta1 \rightarrow 3Gal\beta1 \rightarrow 4Glc\beta1 \rightarrow 1Cer$$
$$\overset{4}{\underset{Fuc\alpha1}{\uparrow}}$$

2. IV$^2$FucLc$_4$ (H type 1)

$$Gal\beta1 \rightarrow 3GlcNAc\beta1 \rightarrow 3Gal\beta1 \rightarrow 4Glc\beta1 \rightarrow 1Cer$$
$$\overset{2}{\underset{Fuc\alpha1}{\uparrow}}$$

3. III$^4$IV$^2$Fuc$_2$Lc$_4$ (Le$^b$)

$$Gal\beta1 \rightarrow 3GlcNAc\beta1 \rightarrow 3Gal\beta1 \rightarrow 4Glc\beta1 \rightarrow 1Cer$$
$$\overset{2}{\underset{Fuc\alpha1}{\uparrow}} \quad \overset{4}{\underset{Fuc\alpha1}{\uparrow}}$$

4. IV$^3$Gal$\beta$1→3GlcNAcnLc$_4$ $$Gal\beta1 \rightarrow 3GlcNAc\beta1 \rightarrow 3Gal\beta1 \rightarrow 4GlcNAc\beta1 \rightarrow 3Gal\beta1 \rightarrow 4Glc\beta1\beta \rightarrow 1Cer$$

5. nLc$_6$ $$Gal\beta1 \rightarrow 4GlcNAc\beta1 \rightarrow 3Gal\beta1 \rightarrow 4GlcNAc\beta1 \rightarrow 3Gal\beta1 \rightarrow 4Glc\beta1\beta \rightarrow 1Cer$$

6. Lc$_6$ $$Gal\beta1 \rightarrow 3GlcNAc\beta1 \rightarrow 3Gal\beta1 \rightarrow 3GlcNAc\beta1 \rightarrow 3Gal\beta1 \rightarrow 4Glc\beta1\beta \rightarrow 1Cer$$

7. III$^3$V$^3$Fuc$_2$nLc$_6$ (dimeric Le$^x$)

$$Gal\beta1 \rightarrow 4GlcNAc\beta1 \rightarrow 3Gal\beta1 \rightarrow 4GlcNAc\beta1 \rightarrow 3Gal\beta1 \rightarrow 4Glc\beta1 \rightarrow 1Cer$$
$$\overset{3}{\underset{Fuc\alpha1}{\uparrow}} \quad \overset{3}{\underset{Fuc\alpha1}{\uparrow}}$$

8. IV$^3$Gal$\beta$1→3[Fuc$\alpha$1→4]GlcNAcnLc$_4$ $$Gal\beta1 \rightarrow 3GlcNAc\beta1 \rightarrow 3Gal\beta1 \rightarrow 4GlcNAc\beta1 \rightarrow 3Gal\beta1 \rightarrow 4Glc\beta1 \rightarrow 1Cer$$
$$\overset{4}{\underset{Fuc\alpha1}{\uparrow}}$$

9. IV$^3$Gal$\beta$1→3GlcNAcIII$^3$FucnLc$_4$ $$Gal\beta1 \rightarrow 3GlcNAc\beta1 \rightarrow 3Gal\beta1 \rightarrow 4GlcNAc\beta1 \rightarrow 3Gal\beta1 \rightarrow 4Glc\beta1 \rightarrow 1Cer$$
$$\overset{3}{\underset{Fuc\alpha1}{\uparrow}}$$

10. IV$^3$Gal$\beta$1→3[Fuc$\alpha$→1→4]GlcNAcIII$^3$FucnLc$_4$ (Le$^a$/Le$^x$)

$$Gal\beta1 \rightarrow 3GlcNAc\beta1 \rightarrow 3Gal\beta1 \rightarrow 4GlcNAc\beta1 \rightarrow 3Gal\beta1 \rightarrow 4Glc\beta1 \rightarrow 1Cer$$
$$\overset{4}{\underset{Fuc\alpha1}{\uparrow}} \quad \overset{3}{\underset{Fuc\alpha1}{\uparrow}}$$

11. III$^4$V$^4$Fuc$_2$Lc$_6$ (dimeric Le$^a$)

$$Gal\beta1 \rightarrow 3GlcNAc\beta1 \rightarrow 3Gal\beta1 \rightarrow 3GlcNAc\beta1 \rightarrow 3Gal\beta1 \rightarrow 4Glc\beta1 \rightarrow 1Cer$$
$$\overset{4}{\underset{Fuc\alpha1}{\uparrow}} \quad \overset{4}{\underset{Fuc\alpha1}{\uparrow}}$$

12. V$^4$FucLc$_6$ $$Gal\beta1 \rightarrow 3GlcNAc\beta1 \rightarrow 3Gal\beta1 \rightarrow 3GlcNAc\beta1 \rightarrow 3Gal\beta1 \rightarrow 4Glc\beta1 \rightarrow 1Cer$$
$$\overset{4}{\underset{Fuc\alpha1}{\uparrow}}$$

13. III$^4$FucLc$_6$ $$Gal\beta1 \rightarrow 3GlcNAc\beta1 \rightarrow 3Gal\beta1 \rightarrow 3GlcNAc\beta1 \rightarrow 3Gal\beta1 \rightarrow 4Glc\beta1 \rightarrow 1Cer$$
$$\overset{4}{\underset{Fuc\alpha1}{\uparrow}}$$

14. Le$^y$ $$Gal\beta1 \rightarrow 4GlcNAc\beta1 \rightarrow 3Gal\beta1 \rightarrow 4Glc\beta1 \rightarrow 1Cer$$
$$\overset{2}{\underset{Fuc\alpha1}{\uparrow}} \quad \overset{3}{\underset{Fuc\alpha1}{\uparrow}}$$

15. Le$^b$/Le$^a$ $$Gal\beta1 \rightarrow 3GlcNAc\beta1 \rightarrow 3Gal\beta1 \rightarrow 3GlcNAc\beta1 \rightarrow 3Gal\beta1 \rightarrow 4Glc\beta1 \rightarrow 1Cer$$
$$\overset{2}{\underset{Fuc\alpha1}{\uparrow}} \quad \overset{4}{\underset{Fuc\alpha1}{\uparrow}} \quad \overset{4}{\underset{Fuc\alpha1}{\uparrow}}$$

TABLE III-continued

Structures of glycolipids with fucosylated lacto-series type 1 and type 2 chain.

16. Le$^y$/Le$^x$ (trifucosyl Le$^y$)

$$Gal\beta1 \xrightarrow{} 4GlcNAc\beta1 \xrightarrow{} 3Gal\beta1 \xrightarrow{} 4GlcNAc\beta1 \xrightarrow{} 3Gal\beta1 \xrightarrow{} 4Glc\beta1 \xrightarrow{} 1Cer$$
$$\overset{2}{\uparrow} \quad \overset{3}{\uparrow} \quad \overset{3}{\uparrow}$$
$$Fuc\alpha1 \quad Fuc\alpha1 \quad Fuc\alpha1$$

17. SLe$^a$-Le$^a$ (extended sialyl-Le$^a$)

$$NeuAc\alpha2 \rightarrow 3Gal\beta1 \rightarrow 3GlcNAc\beta1 \rightarrow 3Gal\beta1 \rightarrow 3GlcNAc\beta1 \rightarrow 3Gal\beta1 \rightarrow 3Glc\beta1 \rightarrow 1Cer$$
$$\overset{4}{\uparrow} \quad \overset{4}{\uparrow}$$
$$Fuc\alpha1 \quad Fuc\alpha1$$

Example 4

MA$_B$IMH2

A. Production

MAb IMH2 was established after immunization of Balb/c mice with Le$^b$/Le$^a$ antigen (Table III, structure 15) isolated from Colo205 cells (isolated as described in Example 2 above) and adsorbed on *Salmonella minnesotae* (adsorption according to Young et al., *J. Exp. Med.* 150:1008–1019, 1979). Forty μg Le$^b$/Le$^a$ was dissolved in 100 μl ethanol and mixed with 1.6 ml PBS (pH 7.4). This solution was combined with 500 μl of a suspension containing 500 μg acid-treated *S. minnesotae* and incubated at 37° C. for 30 min with occasional shaking. The suspension was freeze-dried, and the dried residue was re-suspended in 2 ml water, divided into 8 vials, and frozen until use. Each vial contained approximately 5 μg of GSL antigen and 62 μg of bacteria in 250 μl PBS. Contents of each vial were injected via tail vein into 6-week-old female Balb/c mice on four occasions, with 10-day intervals. Two mice were immunized at a given time. Three days after the last injection, splenocytes of immunized mice were harvested and fused with NS/1 myeloma cells according to the procedure originally described by Young et al. (*J. Exp. Med,* 150:1008–1019, 1979). Hybridomas were selected using 96-well plates coated with phosphatidylcholine-cholesterol-Le$^b$/Le$^a$ 5:3:1 by weight. The quantity of Le$^b$/Le$^a$ added was approximately 50 ng/welL Reactivity was determined by ELISA assay. Clones showing preferential reactivity with the itnmunogen were subcloned repeatedly until a stable clone was established. The isotype of MAb IMH2 was determined to be IgG$_3$.

B. Imm-unochemical Characterization of MAb IMH2 Epitope

The binding specificity of MAb IMH2 was tested by thin-layer chromatography immunostaining of various GSL antigens by the method previously described by Magnani et al. (*Anal. Biochem.* 109:399–402, 1980), and modified by Kannagi et al. (*Cancer Res.* 43:4997–5005, 1983). IMH2 reactivity was also determined by antibody binding on solid-phase antigen as follows. Each GSL antigen, dissolved in ethanol (100 ng/50 μl), was placed in a well, serially diluted with ethanol to 0.1 ng/50 μl per well in a flat-bottom 48-well plate (Falcon, Becton-Dickinson, Lincoln Park, N.J.), and dried. The dried antigen in each well was then incubated with 1% bovine serum albumin in PBS for 1 hr at room temperature, followed by reaction with IMH2 (5 μg/ml) for 18 hr at 4° C. Each well was washed with PBS, followed by incubation with biotinylated second antibody and avidin-peroxidase conjugate as prepared in the ELISA assay kit. The orange color developed in each well was read by automated "ELISA reader" (EL312 Biokinetics Reader, Biotek Instruments, Winooski, Vt.), and optical density at 490 mm for each well was recorded.

Figure 8B:
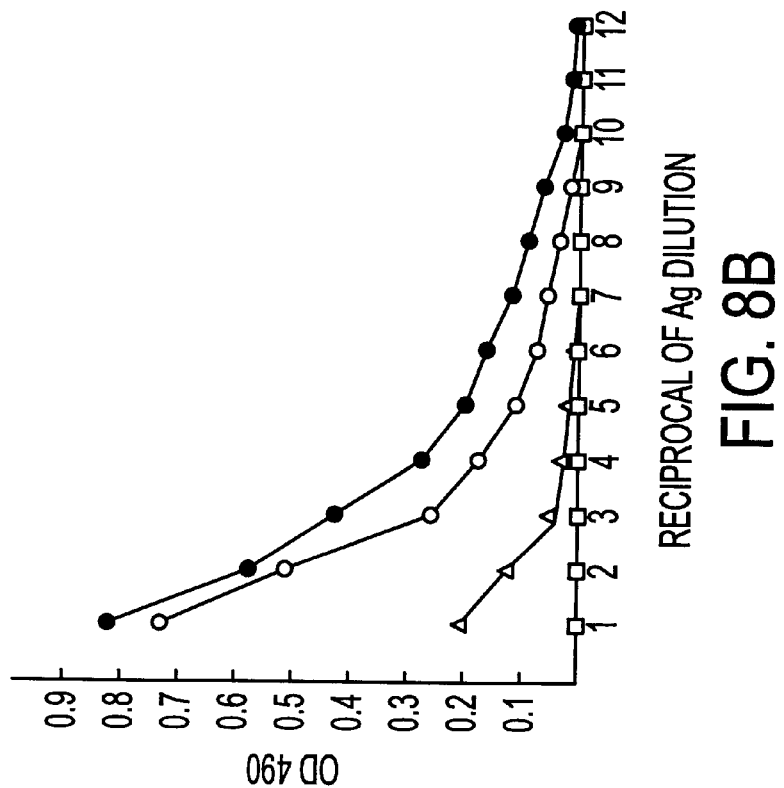
FIG. 8 graphically illustrates the reactivity of MAb IMH2 with various glycosphingolipids (GSLs). Serial double dilutions of various GSL antigens were added to 96-well flat-bottom assay plates (Probind plate, Falcon) in ethanol and dried. Initial concentration of GSL added to the first well was 100 ng/well. MAb binding assay was performed by ELISA as described below. Abscissa, reciprocal of antigen dilution. Ordinate, optical density reading at 490 nm. Paraglboside is abbreviated as "PG". Panel A: reactivity of type 1 chain GSLS. ●, Le$^b$/Le$^a$. ○, Le$^b$ hexasaccharide (IV$^2$FucIII$^4$FucLc$_4$). △, Le$^a$/Le$^a$. □ (all of the following showed similar reactivity), type 1 chain PG (Lc$_4$); H$_1$ type 1 chain (IV$^2$FucLc$_4$); Le$^a$/Le$^x$ (IV$^3$Galβ1→3[Fucα1→4] GlcNAcβIII$^3$FucnLc$_4$). Panel B: reactivity of type 2 chain GSLs. ●, Le$^y$/Le$^x$ (VI$^2$FucV$^3$FucIII$^3$FucnLc$_6$). ○, Le$^y$ hexasaccharide ceramide (IV$^2$FucIII$^3$FucnLc$_4$). △, Le$^x$/Le$^x$ (V$^3$FucIII$^3$FucnLc$_6$). □ (all of the following had similar reactivity), H$_1$ type 2 chain (IV$^2$nLc$_4$); H$_2$ type 2 chain (IV$^2$FucnLc$_6$); PG (nLc$_4$); Le$^x$ (III$^3$FucnLc$_4$). When GSL antigens were mixed with cholesterol and phosphatidylcholine in a molar ratio of 1:5:3 in ethanol and analyzed as above, the relative degrees of reactivity were essentially the same as shown in the figure.
Figure 8A:
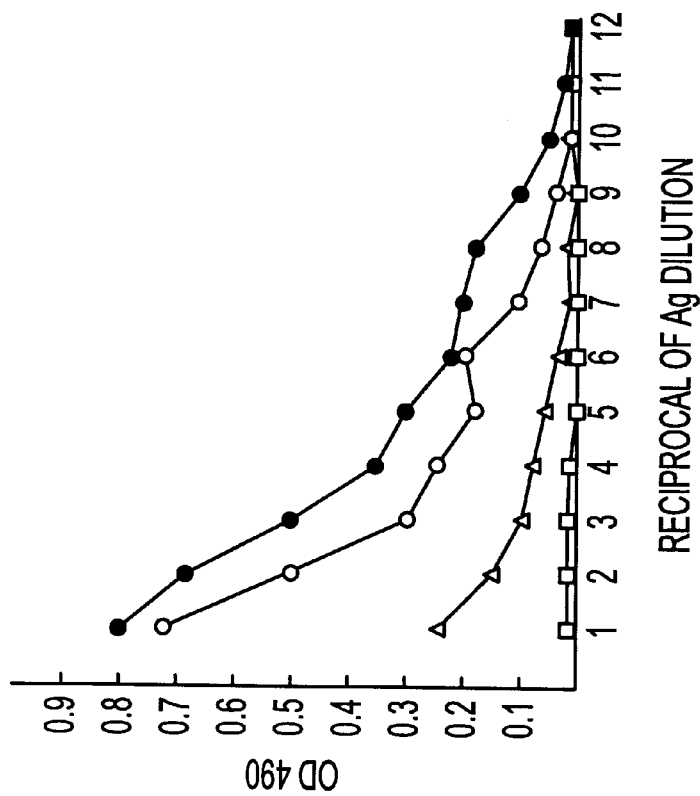

Studies on IMH2 binding (Table IV) to various GSL structures (Table III) revealed that the MAb reacts strongly with Le$^b$/Le$^a$ (structure 15; FIG. 8A) as well as Le$^y$/Le$^x$ (structure 16; FIG. 8B). It also reacted, but more weakly, with hexasaccharide ceramide having Le$^y$ (structure 14) or Le$^b$ (structure 3) determinants (FIG. 8). It reacted weakly with Le$^a$/Le$^a$ antigen (FIG. 8A), but did not react with Lc$_4$, H type 1 chain (IV$^2$FucLc$_4$), Le$^a$/Le$^x$ (FIG. 8A), H$_1$ (IV$^2$FucnLc$_4$), H$_2$ (VI$^2$FucnLc$_6$), Le$^x$ (III$^3$FucnLc$_4$), or nLc$_4$ (FIG. 8B). IMH2 reacted equally well with Le$^y$/Le$^x$ (VI$^2$FucV$^3$FucIII$^3$FucnLc$_6$) as with Le$^b$/Le$^a$, and reacted weakly with Le$^x$/Le$^x$ (V$^3$FucIII$^3$FucnLc$_6$) (FIG. 8B).

TABLE IV

Reactivity of MAb IMH-2 with various glycosphingolipid (GSL) antigens.

| GSL | IHM-2 Reactivity |
| --- | --- |
| Le$^a$/Le$^a$ | − |
| Le$^b$/Le$^a$ | ++ |
| Le$^y$/Le$^x$ | ++ |
| Le$^x$/Le$^x$ | − |
| Le$^a$/Le$^x$ | − |
| Le$^y$ | + |
| Le$^b$ | + |

Anomeric protons for two fucoses F$_V$-1 and F$_{III}$-1 of extended Le$^a$ (or SLe$^a$–Le$^a$) showed a sharp spectrum at 4.8 ppm which is quite distinct from type 1 chain anomeric spectrum of fucoses linked to type 2 chains. All other spectrum for anomeric protons of III GlcNAc, IV GlcNAc, V GlcNAc and VI Gal are distinctly different from type 2 chains. These characteristics are in accordance with typical type 1 chains as described above in Example 3, Item B.

C. In vitro Cytotoxicitv of IMH2

1. Cell Lines

Colo205 was originally obtained from American Type Culture Collection (ATCC) and cultured in RPMI-1640 medium supplemented with 10% fetal calf serum, 1 mM L-glutamine, 100 IU/mi penicillin, and 10 μg/ml streptomycin. Human epidermoid carcinoma A431 cell line (MacLeod et al., *J. Cell. Physiol.* 127:175–182, 1986) was originally donated by Dr. Carol MacLeod (Gildred Cancer Facility, UCSD School of Medicine. San Diego, Calif.). This cell line expresses Le$^a$, Le$^b$, Le$^x$, Le$^y$, and ALe$^b$ on the EGF receptor (Gooi et al., *Biosci. Reports* 5:83–94, 1985). A431 cells were cultured in Dulbecco's modified Eagle's medium (Irvine Scientific, Santa Ana, Calif.) supplemented with 5% fetal calf serum, 1 mM glutamine, 110 mg/l sodium pyruvate, 100 IU/ml penicillin, and 10 μg/ml streptomycin. Cells (about 5×10$^5$/ml) were seeded and harvested at confluency by EDTA treatment followed by washing with PBS containing Ca$^{2+}$ and Mg$^{2+}$. These were used as target cells in in vitro cytotoxdcity assay, or used for testing tumorigenicity in nude mice by subcutaneous inoculation of 5×10⁶ cells. Human erythroleukemia K562 cells (Lozzio et al., *Blood* 45:321–334, 1975) were used as controls for natural killer (NK) activity of lymphocytes used in the assay system.

2. Antibody-Dependent Cellular Qtotoxicity (ADCC) and Complement-Dependent Qtotoxicity (CDC)

For the ADCC assay, human peripheral blood leukocytes (HBBL) (used as effector cells) were obtained from bufly coat fraction of blood from healthy volunteer donors. Briefly, mononuclear cells were separated by centrifugation through Ficoll-Hypaque gradient solution at 2000 rpm for 20 min (Mishell et al., in Mishell, B. B and Shiigi, S. M. (eds.), *Selected Methods in Cellular Immunology*, pp. 3–27, W. H. Freeman & Co., San Francisco, Calif., 1980). Mouse splenocytes and mouse peritoneal macrophages (effector cells) were prepared as previously described by Mishell et al., with some modification as follows. Target cells (5×10⁶) were labeled by incubation with 100 μl of $^{51}$Cr for 90 min at 37° C. After washing (3×) and incubation (1 hr at 37° C.), cells (1×10⁶ ml) were suspended in RPMI-1640 supplemented with 25 mM HEPES buffer and 3% bovine serum albumin. Twenty μl of labeled cells, 100 μl of IMH2 or ST-421, ad 100 μl of effector cell suspension were mixed into Microtiter U-bottom plates (Corning, N.Y.). Non-specific mouse Ig (Sigma, St. Louis, Mo.) was used as a negative control. After 4 hr incubation, the plates were centrifuged (500×g, 2 min) with a hanging plate-holder assembled in a centrifuge, and radioactivity in 100 μl supernatant in each well was measured with a gamma counter. Each experimental group was tested in triplicate. Percent specific lysis was calculated according to the formula ([A−B]×100)/C, where A=cpm in lysed experimental cells; B=cpm in unlysed target cells; C=cpm in total target cells. Spontaneous release never exceeded 15% of maximally releasable labeled radioactivity.

For CDC, $^{51}$Cr-release assay was performed using a procedure similar to that for ADCC, except that 100 μl of diluted human serum was added as a complement source instead of effector cells. The serum was inactivated at 56° C. for 30 min and used as a control. Percent specific lysis was calculated as described above.

Figure 9A:
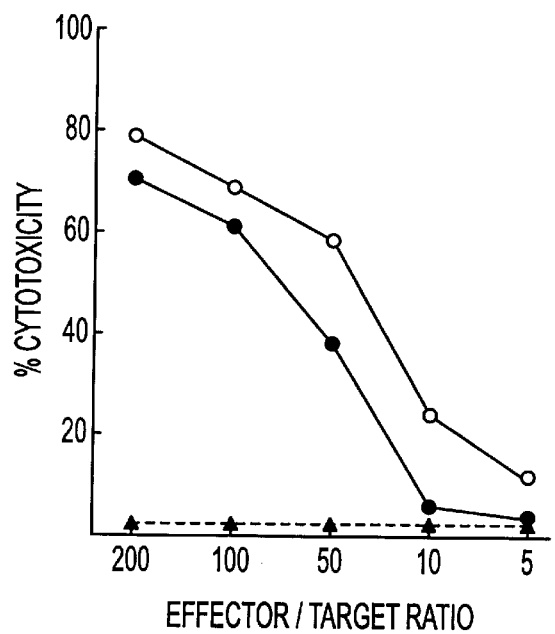
FIG. 9 graphically illustrates the MAb-dependent cytotoxic effect on Colo205 cells by MAbs IMH2 and ST-421. Panel A: cytotoxic effects at various E:T (effector:target cell) ratios. MAbs IMH2 and ST421 were purified and applied at a concentration of about 30 μg/ml. $^{51}$Cr-labeled Colo205 cells were incubated with different ratios of human peripheral blood leukocytes (HPBL) as effectors. At higher E:T ratios, lysis was more conspicuous for both IMH2 and ST-421. ○, ST-421. ●, IMH2. ▲, control mouse IgG and D11G10 (IgG$_3$ anti-Gg3) as non-specific MAbs. Panel B: dependent of cytotoxic effect on MAb concentration at constant E:T ratio 100:1. Maximal cytotoxic effect was observed at a MAb concentration of 35–70 μg/ml. Control MAb D11G10 (○) showed no cytotoxic effect. Panel C: cytotoxic effect with mouse splenocytes as effector cells. Experimental conditions as in Panel A. $^{51}$Cr-labeled Colo205 cells were incubated with various ratios of mouse splenocytes as effector cells. ○, ST-421. ●, IMH2. △, control MAb (D11G10).
Figure 9B:
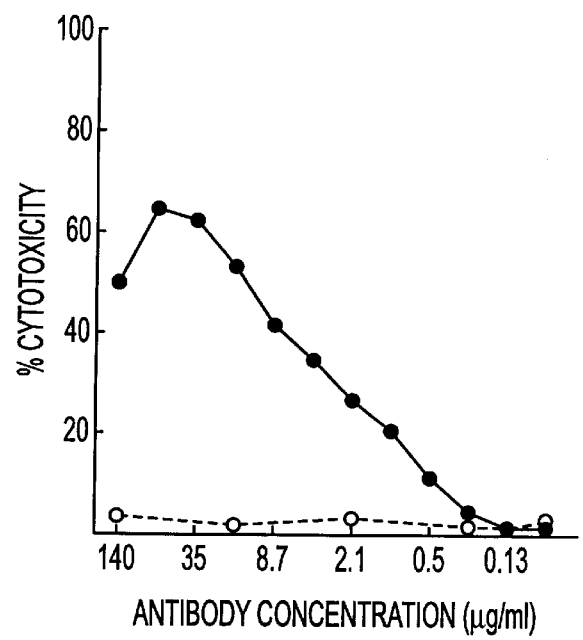
Figure 9C:
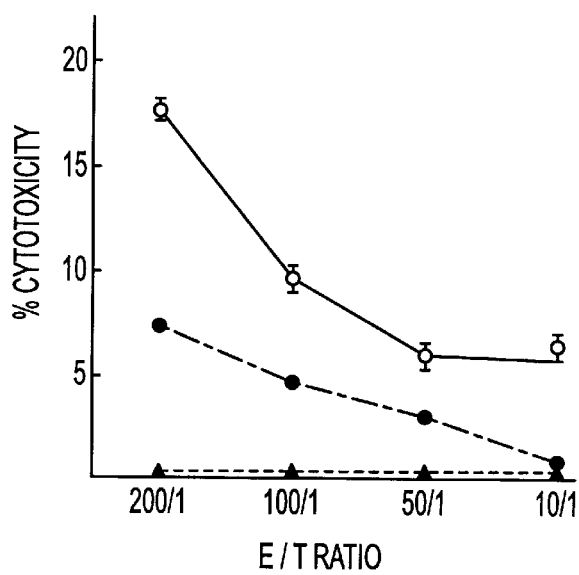
Figure 10B:
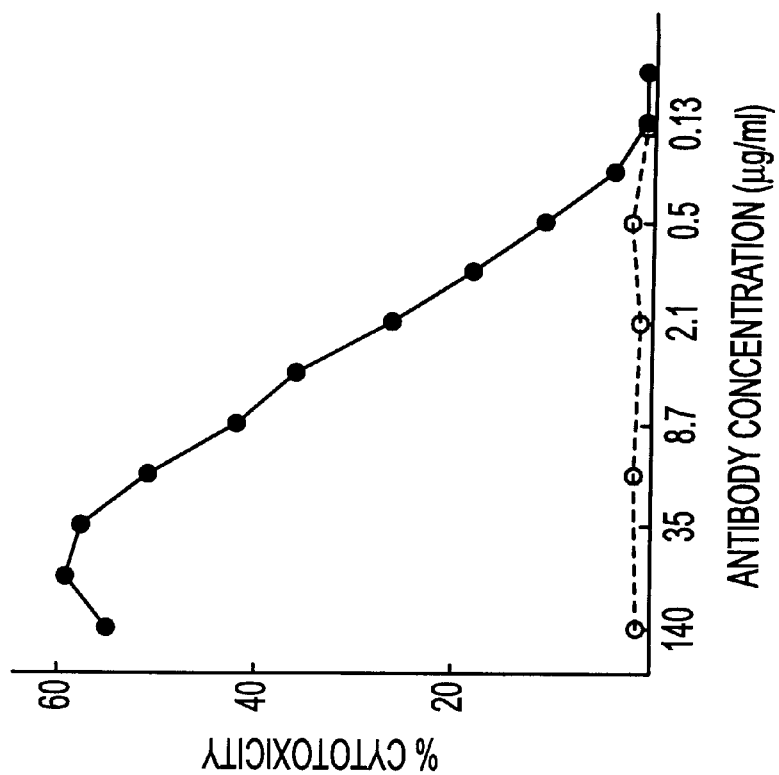
FIG. 10 graphically illustrates the CDC (complement-dependent cytotoxicity) effect on Colo205 cells by MAb IMH2. Fresh human serum was used as complement source. Panel A: $^{51}$Cr-labeled Colo205 cells were incubated with about 30 μg/ml of purified IMH2 or ST-421 and various concentrations of complement (see abscissa). ○, ST-421. ●, IMH2. ▲, control mouse IgG$_3$ with complement. Panel B: $^{51}$Cr-labeled Colo205 cells were incubated with different concentrations of IMH2 (see abscissa) in the presence of 1:4 diluted human serum as a complement source. ●, IMI2. ○, control mouse IgG$_3$ with complement.
Figure 10A:
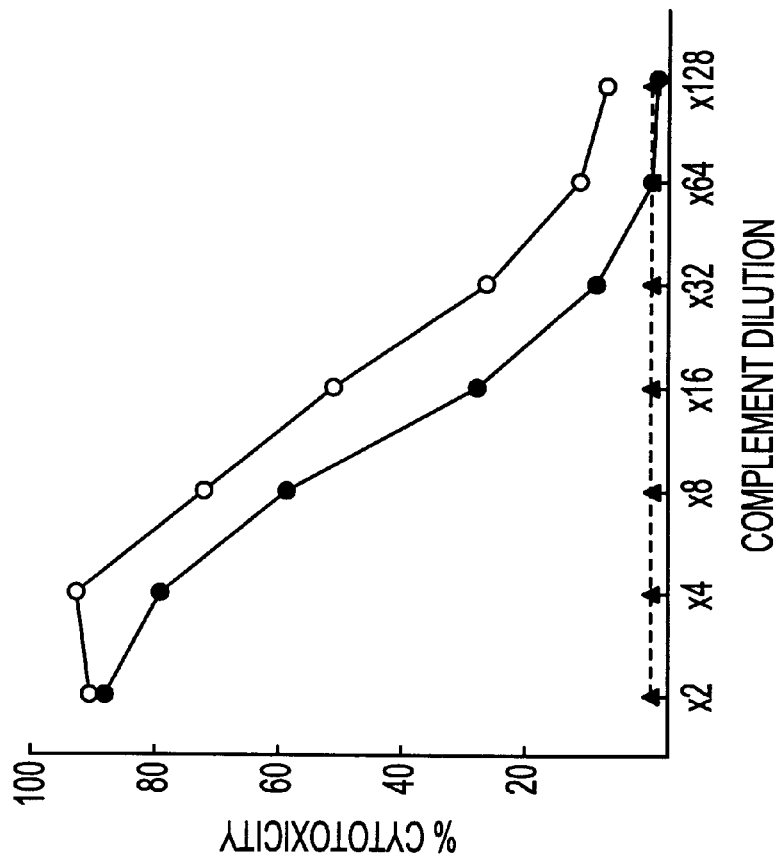

Since Colo205 cells have been characterized as expressing extended type 1 chain Le$^a$/Le$^a$ and Le$^b$/Le$^a$ antigens, which react strongly with MAbs ST-421 and IMH2, respectively, cytotoxic effect of IMH2 against Colo205 was evaluated and compared to that of ST-421. Both MAbs showed strildng ADCC killing of Colo205 cells. This killing was correlated with effector:target cell (E:T) ratio (FIG. 9A) and with MAb concentration (FIG. 9B). The cytotoxic effect was maximal at an E:T ratio of 100:1–200:1, and at a MAb concentration of 35–70 μg/ml. Control mouse IgG and other non-specific MAbs showed no cytotoxic effect regardless of E-T ratio or MAb concentration (FIGS. 9A, 9B). When the same cytotoxicity test was performed with mouse splenocytes, the corresponding values were only 7% and 17% lysis (E:T ratio 200:1, MAb concentration 30 μg/ml) (FIG. 9C). The MAbs showed a weak cytotoxic effect against A431 cells (Table V). Comparison of maximum IMH2-dependent lysis of Colo 205, A431, and K562 cells is shown in Table V. High lysis values (e.g., 65% and 94% lysis of Colo205 cells with IMH2 and ST421, respectively) were only pronounced in the presence of HPBL; values were much less with moiise splenocytes, as observed previously with ST-421 (Watanabe et al., *Cancer Res.* 51:2199–2204, 1991). CDC mediated by IMH2 and ST-421 was similarly correlated with complement concentration (FIG. 10A) and with MAb concentration (FIG. 10B).

TABLE V

MAb-dependent cytotoxic effect on Colo205, A431, and K562 cells by MAbs ST-421 and IMH2.

| Target Cell | Antibody/Reactivity[b] | Percent lysis[a] eff. cell + MAb + | eff. cell + MAb − | eff. cell − MAb + |
|---|---|---|---|---|
| Colo205 | ST-421 + | 94.5 | 2.7 | 0.8 |
|  | IMH2 + | 65.0 | 2.7 | 0.7 |
| A431 | ST-421 ± | 14.4 | 10.9 | 1.1 |
|  | IMH2 ± | 7.6 | 9.2 | 0.6 |
| K562[c] | ST-421 − | 48.2 | 36.2 | 0.5 |
|  | IMH2 − | 44.8 | 36.2 | 0.3 |

[a]Percent lysis at E:T (effector:target cell) ratio of 100:1 with IMH2 (35 μg/ml) and ST-421 (x100 diluted ascites).
[b]Determined by flow cytometry. +, positive; ±, weakly positive; −, negative.
[c]The high cytotoxic effect of K562 cells is also observed in the absence of MAb, and is considered to reflect natural killer cell activity.

D. In vivo Tumor Suppression

Colo205 and A431 cells used for in vivo experiments were grown in vitro, washed 2× with medium, and reconstituted at the desired cell density in PBS. Cells (5×10⁶/100 μl) were subcutaneously injected into the backs of 5- to 7-week-old athymic Balb/c mice, and intraperitoneal administration of MAb was started immediately after injection. Purified IMH2 (1.1 mg/ml) or ST421 in ascites fluid with corresponding concentration of IgG (1.1–1.2 ng/ml) at a dosage of 0.2 ml/animal were intraperitoneally injected 1×/day for 2 weeks. Width and length of tumors were measured by the same observer 3×/week. Tumor weight was estimated as (width²×length)/2. Control aninials received ascites protein produced by mouse myeloma cell line NS1 in Balb/c mice. Seven mice per group were used for each experiment, and experiments were run in duplicate. Mean values of tumor weight based on the duplicate experiments were plotted.

Figure 11:
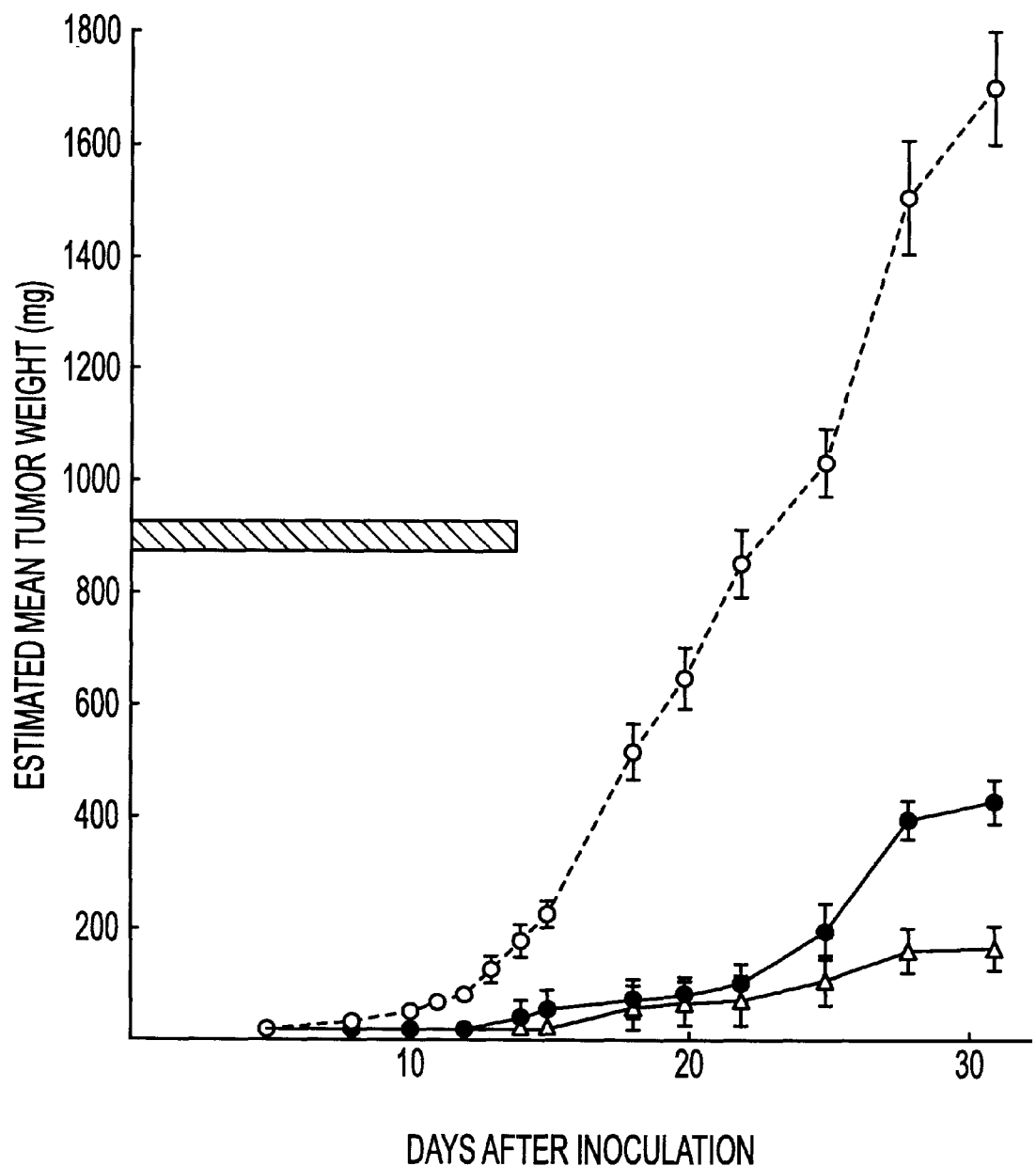
FIG. 11 graphically illustrates the inhibitory effect of MAb IMH2 on Colo205 cell growth in nude mice. Colo205 cells (1×10$^7$) were subcutaneously injected into the backs of 6-week-old athymic Balb/c mice, followed immediately by injection of 200 μl (≈200 μg) of purified IMH2 (1.1 mg/ml) per day for 14 days (shaded bar) (●). Other mice were treated similarly with MAb ST421 (△). Control groups were injected with PBS containing similar quantities of non-specific mouse IgG (○).
Figure 12A:
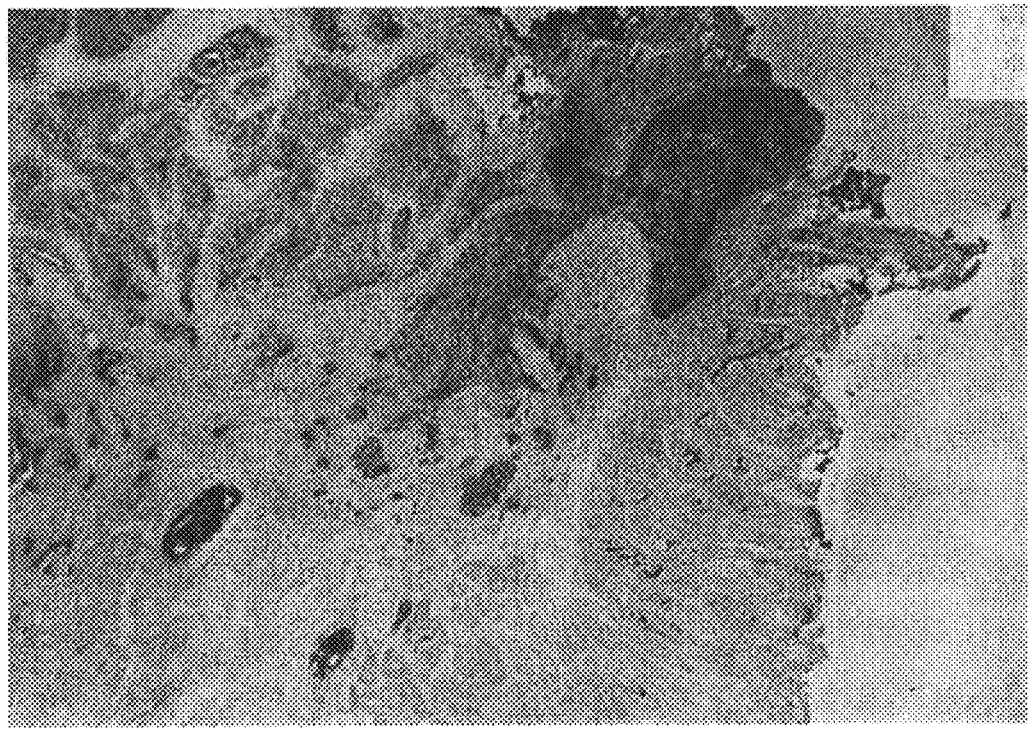
FIG. 12 pictorially depicts immunohistological patterns of various human carcinoma tissues stained by MAb IMH2. A colonic carcinoma, x100. B, colonic carcinoma, x160. C, lung adenocarcinoma, x100. D, liver metastasis from colonic adenocarcinoma. E, F, endometrial carcinoma, x100. It is noted that in each panel adjacent normal tissues were not stained.
Figure 12B:
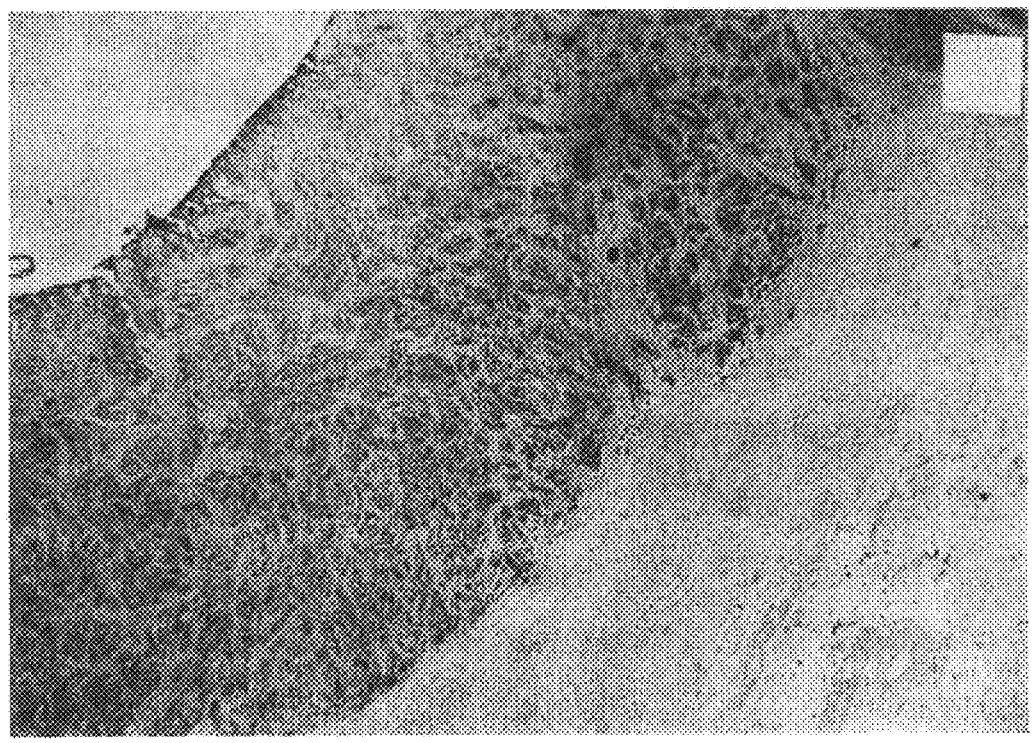
Figure 12C:
Figure 12D:
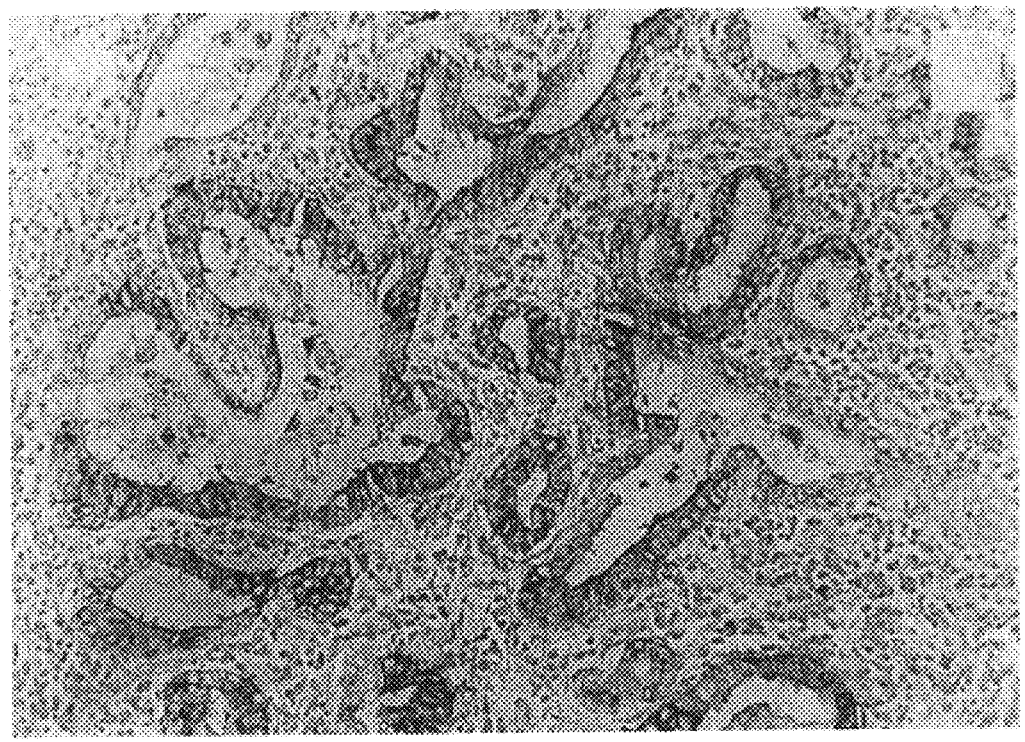
Figure 12E:
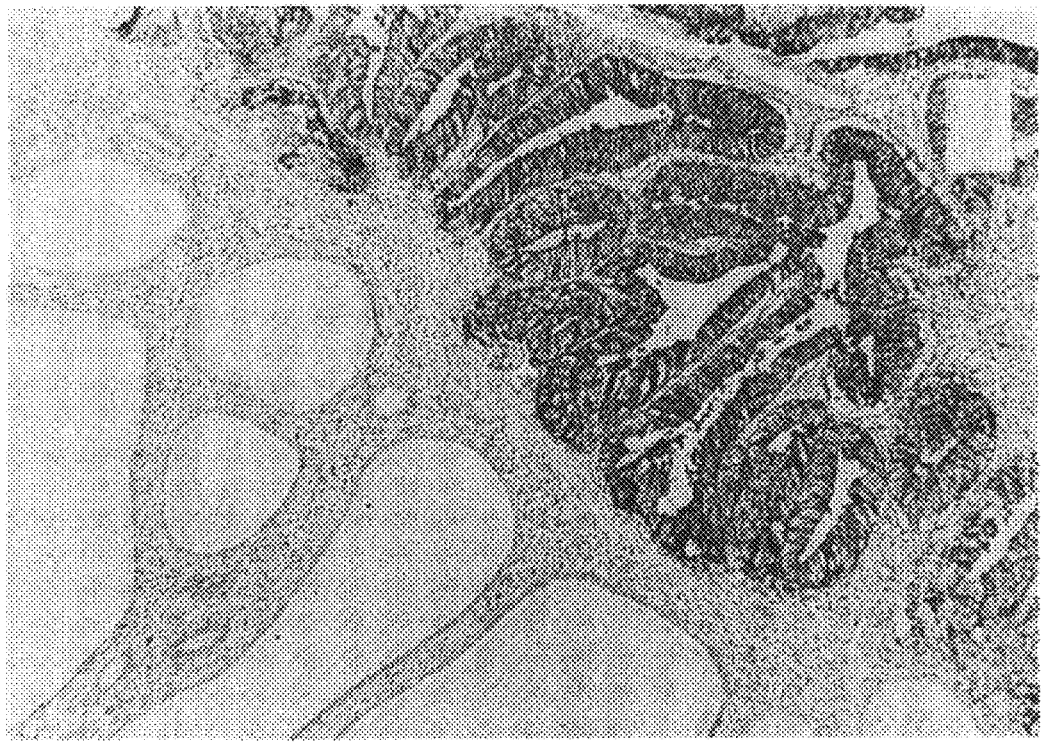
Figure 12F:
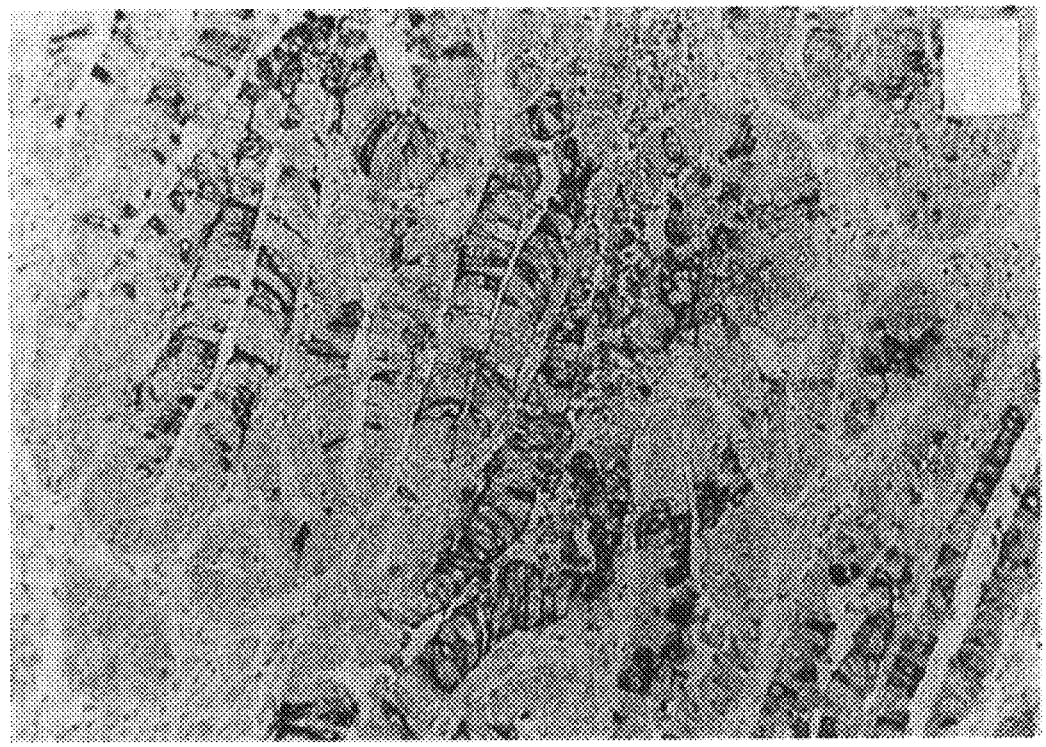

Both MAbs IMH2 and ST-421 showed striking inhibition of Colo205 tumor growth in nude mice (FIG. 11). In contrast, both MAbs showed minimal inhibitory effect on A431 tumor growth. Thus, high expression of the defined antigen appears to be essential for susceptibility to antibody-dependent inhibition of tumor growth in vivo.

E. Reactivity of IMH2 With Various Tumors and Normal Tissues

Various tumors and adjacent normal tissues were obtained from surgical specimens fixed with formalin and paraffin-embedded. In addition, normal tissues and some tumor tissues from brain, thymus, lung, liver, stomach, colon, kidney, adrenal gland, spleen, pancreas, uterus (with endometrium), and skin were obtained by fresh necropsy from accident victims. Both surgical and necropsy specimens were provided through the courtesy of the Department of Pathology, Swedish Medical Center, Seattle, Wash., and Ms. Debbie Bennett of The Biomembrane Institute. Samples were sectioned (3 μM thickness), deparaffinized with xylene, dehydrated in ethanol, treated with primary MAb, subsequently treated with biotinylated secondary MAb and peroxidase-conjugated avidin, and stained with 3', 3'-diaminobenzidine. Endogenous peroxidase activity was blocked by treatment of sections with 0.3% $H_2O_2$ for 20 min. Some sections were incubated with mouse IgG as a negative control. Biotinylated goat anti-mouse IgM, avidin, and biotin were from Vectastain (Burlingame, Calif.).

MAb IMH reacted strongly and with high incidence with tumors from colon, rectum, liver, pancreas, and endometrium (Table VI). In contrast, it showed no reactivity with normal mucosae of distal colon and rectum, including crypt regions and goblet cells. It reacted with lung adenocarcinoma, but not with large cell or small cell carcinoma One out of 5 cases of squamous cell carcinoma showed strong positive reactivity. MAb IMH2 did not react with tissues of normal brain, lung, spleen, skin, or with various blood cells including granulocytes.

Observed locations of normal tissues with strong staining were as follows: Hassall's bodies and epithelial reticular cells of thymus (thymocytes were negative); mucous epithelium and secretory glands of gastric mucosa (lamina propria, serosa, and muscle layer were negative); both medulla and cortex of adrenal glands. Locations of normal tissues with moderate to weak positive staining were: epithelial cells of proximal and distal convolutions of kidney (other parts were negative); cells in Langerhans' islets in pancreas (other parts of pancreas were negative); cecal mucosa; urothelium. Very weak staining was observed for hepatocytes (other parts of liver, infralobular connective tissue, central vein, bile duct, and Kupffer's cells were negative). These results are summarized in Table VI, and some typical positive staining patterns are shown in FIG. 12.

TABLE VI

Immunohistological staining by MAb IMH2 of normal tissues and carcinomas.

| Tissue | Staining | Localization/comments |
|---|---|---|
| Normal | | |
| brain | − | |
| lung | − | including broncheolar epithelia |
| spleen | − | |
| rectum | − | including crypt area |
| colon | − | −11/12, ±1/12 |
| cecum | + | |
| skin | − | |
| granulocytes | − | |
| lymphocytes | − | |
| pancreas | + | + in islets of Langerhans; others − |
| liver | ± | faintly +/± hepatocytes; others −− |
| thymus | ++ | ++ in Hassal's bodies, epithelial and reticular cells; − in thymocytes |
| stomach | +++ | mucosa, glandular cells (see text) |
| kidney | + | weakly + in tubular epithelia (see text) |
| adrenal glands | +++ | |
| uterus/endometrium | −/+ | − or weakly + in endometrium; −9/15, ±2/15, +4/15 (total positive cases 4/15 = 27%) |
| Carcinomas | | |
| colon/rectum | +/+++ | +++4, ++6, +4, ±1, −1 (total positive cases 14/16 = 88%) |
| liver (primary) | ++ | 2/3 |
| pancreas | +++ | 2/2 |
| lung adenocarcinoma | ++ | 2/4 |
| squamous | + | 1/5 |
| large cell | − | 0/3 |
| small cell | − | 0/5 |
| endometrium | −/+++ | +++4, ++11, +6/24, ±/−3 (total positive cases 21/24 = 88%) |

F. Reactivity of IMH2 With Normal and Maliegnant Colonic and Bladder Tissues From Patients With Known Lewis and Secretor Status Expression of $Le^b$ and $Le^y$ determinants is correlated with secretor status of the individual (Sakamoto et al., *Molec, Immun.* 21:1093–1098, 1984; Ørntoft et al., *J. Urol* 138:171–176, 1987), whereas expression of Lewis antigens in some tumors is unrelated to host Lewis status (Ørntoft et al., *Lab. Invest.* 58:576–583, 1988; Ørntoft et al., *Blood* 71:1389–1396, 1991). Therefore, reactivity of MAb IMH2 with normal and malignant colonic and bladder tissues from patients with known Lewis and secretor status was studied. Results are summarized in Tables VII and VIII. IMH2 was reactive with rectal tumors but not with normal rectal tissue, and this reactivity was unrelated to secretor status. Conversely, IMH2 was reactive with normal cecum but less so with the single cecal tumor sample studied. These results suggest that the trend of IMH2 epitope expression in normal and malignant colonic tissues is similar to the well-established expression pattern of ABH antigens. Genuine Lewis-negative ($Le^{a-b-}$) individuals (Ørntoft et al., *Lab. Invest,* 58:576–583, 1988), expressed IMH2 epitope in both normal and malignant colonic tissues (Tables VII and VIII).

IMH2 epitope is expressed in normal urothelium, but its expression is diminished to varying degrees in bladder tumors. There seems to be a correlation with grade of atypia, i.e., IMH2 epitope expression is lowest in highly invasive tumors. Again, this trend is similar to that of ABH antigen expression in normal and malignant bladder tissues. However, in contrast to colonic tissues, IMH2 epitope expression in bladder tissues from blood group A individuals is correlated with secretor status. Genuine Lewis-negative ($Le^{a-b-}$) individuals expressed IMH2 epitope in both normal and malignant bladder tissues.

TABLE VII

Immunohistological staining by MAb IMH2 of normal and malignant colonic tissues: Relationship with host Lewis status.

| | Normal | | Malignant | |
|---|---|---|---|---|
| | rectum | cecum | rectum | cecum |
| A $Le^{a-b+}$ | 0/5 | 1/1 | 3/4 | 1/1 |
| A $Le^{a+b-}$ | 0/4 | ND | 2/2 | ND |
| O $Le^{a-b+}$ | 0/2 | ND | 2/3 | ND |
| O $Le^{a+b-}$ | 0/2 | ND | 1/1 | ND |
| genuine $Le^{a-b-}$ | 0/1 | 1/1[a] | 1/1 | 0/1 |
| non-genuine $Le^{a-b-}$ | 0/2 | ND | 1/1 | 0/1 |

Figures indicate positive specimens divided by total specimens examined. ND = not determined. For $Le^{a-b-}$ individuals (genuine and non-genuine), phenotypic status was determined by α1→4 fucosyltransferase activity in saliva, and erythrocyte reactivity with anti-$Le^a$ and −$Le^b$ MAbs. Definitions of phenotypes may be found in Holmes et al., Arch. Biochem. Biophys. 274:14–25, 1989, and Ørntoft et al., Lab. Invest. 58:576–583, 1988.
[a]Non-secretor.

TABLE VIII

Immunohistological staining by MAb IMH2 of normal and malignant bladder tissues: Relationship with host Lewis status.

| | | Bladder carcinoma | |
|---|---|---|---|
| | normal | noninvasive | invasive |
| A $Le^{a-b+}$ | 4/4 | 1/1 | 1/2 |
| A $Le^{a+b-}$ | 0/2 | 1/2 | 1/3 |
| O $Le^{a-b+}$ | 1/1 | 1/1 | 1/2 |
| O $Le^{a+b-}$ | 2/2 | 1/1 | 0/1 |
| genuine $Le^{a-b-}$ | 2/2 | ND | 0/1 |
| non-genuine $Le^{a-b-}$ | ND | ND | ND |

Main footnote as for Table VII.

From the foregoing, it will be evident that, although specific embodiments of the invention have been described herein for purposes of illustration, various modification may be made without deviating from the spirit and scope of the invention.

We claim:

1. An isolated compound having the formula:

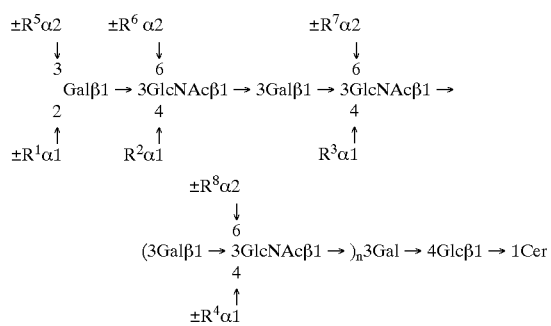

wherein $R^1$, $R^2$, $R^3$ and $R^4$ are fucosyl residues; $R^5$, $R^6$, $R^7$ and $R^8$ are sialyl residues, provided that $R^1$ and $R^5$ are not present together; n is 0 or an integer of 1 or more; when n is 1, the compound has 1 or more sialyl residues; Gal is galactose, GlcNAc is N-acetylglucosamine, Glc is glucose and Cer is ceramide.

2. The isolated compound of claim 1, wherein there are at least two sialyl residues.

3. The isolated compound of claim 1, having the formula:

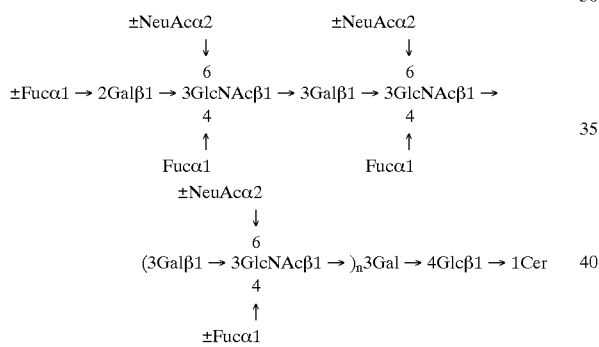

wherein Fuc represents fucose and NeuAc represents N-acetylneuraminic acid.

4. The isolated compound of claim 1 having the formula:

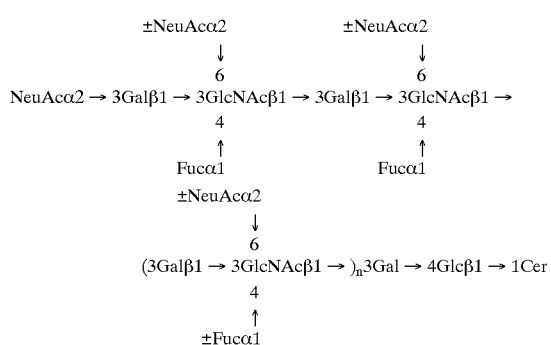

wherein Fuc represents fucose and NeuAc represents N-acetylneuraminic acid.

5. The isolated compound of claim 1 having the formula:

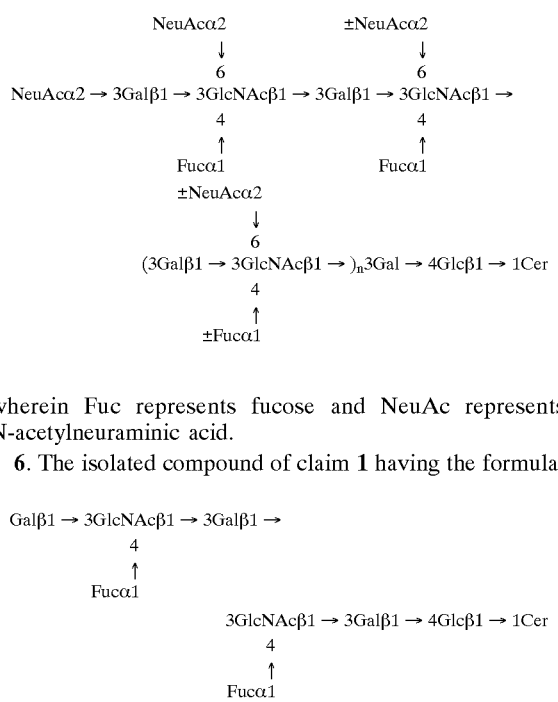

wherein Fuc represents fucose and NeuAc represents N-acetylneuraminic acid.

6. The isolated compound of claim 1 having the formula:

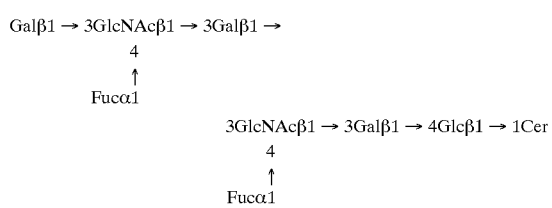

wherein Fuc represents fucose.

7. The isolated compound of claim 1 having the formula:

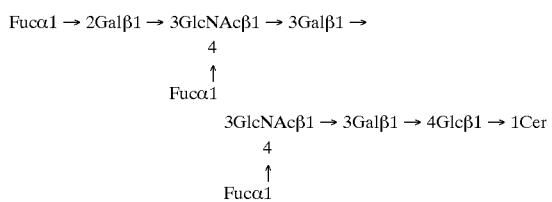

wherein Fuc represents fucose.

8. The isolated compound of claim 1 having the formula:

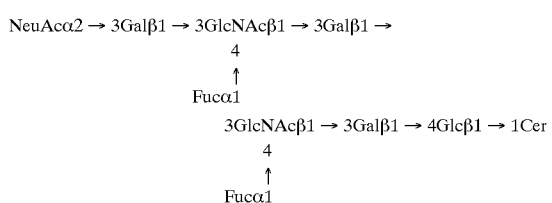

wherein NeuAc represents N-acetylneuraminic acid, and Fuc represents fucose.

9. A pharmaceutical composition comprising an adjuvant and either (a) an isolated glycolipid or glycoprotein compound comprising an epitope having a formula

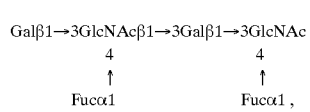

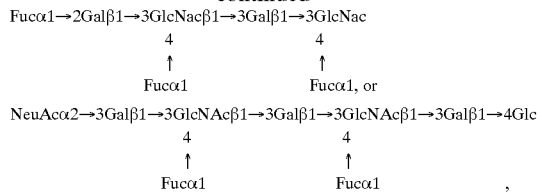
wherein NeuAc represents N-acetylneuraminic acid, Gal represents galactose, GlcNAc represents N-acetylglucosamine, Glc represents glucose, and Fuc represents fucose, or
(b) the compound of any one of claims 1–8.
* * * * *